(12) United States Patent
Smiley

(10) Patent No.: US 12,370,040 B2
(45) Date of Patent: *Jul. 29, 2025

(54) ADJUSTABLE INTRAOCULAR LENSES AND METHODS OF POST-OPERATIVELY ADJUSTING INTRAOCULAR LENSES

(71) Applicant: Alcon Inc., Fribourg (CH)

(72) Inventor: Terah Whiting Smiley, Davis, CA (US)

(73) Assignee: Alcon Inc., Fribourg (CH)

( * ) Notice: Subject to any disclaimer, the term of this patent is extended or adjusted under 35 U.S.C. 154(b) by 248 days.

This patent is subject to a terminal disclaimer.

(21) Appl. No.: 17/823,822

(22) Filed: Aug. 31, 2022

(65) Prior Publication Data

US 2022/0409363 A1 Dec. 29, 2022

Related U.S. Application Data

(63) Continuation of application No. 17/060,940, filed on Oct. 1, 2020, now Pat. No. 11,471,272.

(Continued)

(51) Int. Cl.
*A61F 2/16* (2006.01)
*A61L 27/44* (2006.01)
*A61L 27/50* (2006.01)

(52) U.S. Cl.
CPC .......... *A61F 2/1624* (2013.01); *A61F 2/1605* (2015.04); *A61F 2/1635* (2013.01); *A61F 2/1659* (2013.01); *A61L 27/44* (2013.01); *A61L 27/443* (2013.01); *A61L 27/50* (2013.01); *A61F 2002/1681* (2013.01);

(Continued)

(58) Field of Classification Search
CPC .... A61F 2/1613; A61F 2/1624; A61F 2/1635; A61F 2/1648; A61F 2/1659; A61F 2002/1682; A61F 2250/0013; A61F 2250/0003; A61F 2250/0053
See application file for complete search history.

(56) References Cited

U.S. PATENT DOCUMENTS

| | | | |
|---|---|---|---|
| 4,111,995 | A | 9/1978 | Nelson |
| 4,251,887 | A | 2/1981 | Anis |

(Continued)

FOREIGN PATENT DOCUMENTS

| | | |
|---|---|---|
| CN | 1283974 | 2/2001 |
| CN | 1367667 | 9/2002 |

(Continued)

OTHER PUBLICATIONS

Baughman et al. "Negative poisson's ratios for extreme states fo matter," Science, vol. 288, pp. 2018-2022, Jun. 16, 2000.

(Continued)

*Primary Examiner* — William H Matthews
(74) *Attorney, Agent, or Firm* — Levine Bagade Han LLP

(57) ABSTRACT

Disclosed are adjustable intraocular lenses and methods of adjusting intraocular lenses post-operatively. In one embodiment, an adjustable intraocular lens can comprise an optic portion and a peripheral portion. The peripheral portion can comprise a composite material comprising an energy absorbing constituent and a plurality of expandable components. A base power of the optic portion can be configured to change in response to an external energy directed at the composite material.

19 Claims, 12 Drawing Sheets

Related U.S. Application Data

(60) Provisional application No. 62/911,039, filed on Oct. 4, 2019.

(52) U.S. Cl.
CPC .................. *A61F 2002/169* (2015.04); *A61F 2002/16901* (2015.04); *A61F 2230/0069* (2013.01); *A61F 2250/0003* (2013.01); *A61L 2300/204* (2013.01); *A61L 2300/442* (2013.01); *A61L 2430/16* (2013.01)

(56) References Cited

U.S. PATENT DOCUMENTS

| | | | |
|---|---|---|---|
| 4,253,199 A | 3/1981 | Banko |
| 4,254,509 A | 3/1981 | Tennant |
| 4,258,311 A | 3/1981 | Tokuda et al. |
| 4,304,895 A | 12/1981 | Loshaek |
| 4,373,218 A | 2/1983 | Schachar |
| 4,409,691 A | 10/1983 | Levy |
| 4,423,809 A | 1/1984 | Mazzocco |
| 4,435,855 A | 3/1984 | Pannu |
| 4,435,856 A | 3/1984 | L'esperance |
| 4,466,705 A | 8/1984 | Michelson |
| 4,490,860 A | 1/1985 | Rainin |
| 4,494,254 A | 1/1985 | Lopez |
| 4,512,040 A | 4/1985 | Mcclure |
| 4,528,311 A | 7/1985 | Beard et al. |
| 4,575,373 A | 3/1986 | Johnson |
| 4,585,457 A | 4/1986 | Kalb |
| 4,604,295 A | 8/1986 | Humphreys |
| 4,615,701 A | 10/1986 | Woods |
| 4,620,954 A | 11/1986 | Singer et al. |
| 4,685,921 A | 8/1987 | Peyman |
| 4,685,922 A | 8/1987 | Peyman |
| 4,693,717 A | 9/1987 | Michelson |
| 4,720,286 A | 1/1988 | Bailey et al. |
| 4,731,078 A | 3/1988 | Stoy et al. |
| 4,731,079 A | 3/1988 | Stoy |
| 4,731,080 A | 3/1988 | Galin |
| 4,764,423 A | 8/1988 | Yamaguchi et al. |
| 4,784,485 A | 11/1988 | Ho |
| 4,787,903 A | 11/1988 | Grendahl |
| 4,790,847 A | 12/1988 | Woods |
| 4,813,956 A | 3/1989 | Gupta |
| 4,816,031 A | 3/1989 | Pfoff |
| 4,836,201 A | 6/1989 | Patton et al. |
| 4,842,601 A | 6/1989 | Smith |
| 4,848,343 A | 7/1989 | Wallsten et al. |
| 4,888,012 A | 12/1989 | Horn et al. |
| 4,892,543 A | 1/1990 | Turley |
| 4,902,293 A | 2/1990 | Feaster |
| 4,913,536 A | 4/1990 | Barnea |
| 4,919,151 A | 4/1990 | Grubbs et al. |
| 4,932,966 A | 6/1990 | Christie et al. |
| 4,946,469 A | 8/1990 | Sarfarazi |
| 4,950,289 A | 8/1990 | Krasner |
| 4,963,148 A | 10/1990 | Sulc et al. |
| 4,994,082 A | 2/1991 | Richards et al. |
| 4,995,879 A | 2/1991 | Dougherty |
| 4,995,880 A | 2/1991 | Galib |
| 5,015,254 A | 5/1991 | Greite |
| 5,035,710 A | 7/1991 | Nakada et al. |
| 5,047,051 A | 9/1991 | Cumming |
| 5,061,914 A | 10/1991 | Busch et al. |
| 5,066,301 A | 11/1991 | Wiley |
| 5,078,740 A | 1/1992 | Walman |
| 5,145,884 A | 9/1992 | Yamamoto et al. |
| 5,145,935 A | 9/1992 | Hayashi |
| 5,152,789 A | 10/1992 | Willis |
| 5,169,920 A | 12/1992 | Okawa |
| 5,171,266 A | 12/1992 | Wiley et al. |
| 5,200,430 A | 4/1993 | Federman |
| 5,201,763 A | 4/1993 | Brady et al. |
| 5,203,788 A | 4/1993 | Wiley |
| 5,213,579 A | 5/1993 | Yamada et al. |
| 5,217,491 A | 6/1993 | Vanderbilt |
| 5,224,957 A | 7/1993 | Gasser et al. |
| 5,235,003 A | 8/1993 | Ward et al. |
| 5,251,993 A | 10/1993 | Sigourney |
| 5,275,623 A | 1/1994 | Sarfarazi |
| 5,275,624 A | 1/1994 | Hara et al. |
| 5,288,293 A | 2/1994 | O'donnell |
| 5,290,892 A | 3/1994 | Namdaran et al. |
| 5,326,347 A | 7/1994 | Cumming |
| 5,391,590 A | 2/1995 | Gerace et al. |
| 5,405,386 A | 4/1995 | Rheinish et al. |
| 5,426,166 A | 6/1995 | Usifer et al. |
| 5,443,506 A | 8/1995 | Garabet |
| 5,444,106 A | 8/1995 | Zhou et al. |
| 5,444,135 A | 8/1995 | Cheradame et al. |
| 5,476,514 A | 12/1995 | Cumming |
| 5,483,305 A | 1/1996 | Kohayakawa |
| 5,489,302 A | 2/1996 | Skottun |
| 5,496,366 A | 3/1996 | Cumming |
| 5,506,300 A | 4/1996 | Ward et al. |
| 5,512,609 A | 4/1996 | Yang |
| 5,567,365 A | 10/1996 | Weinschenk et al. |
| 5,578,081 A | 11/1996 | Mcdonald |
| 5,585,049 A | 12/1996 | Grisoni et al. |
| 5,593,436 A | 1/1997 | Langerman |
| 5,607,472 A | 3/1997 | Thompson |
| 5,628,795 A | 5/1997 | Langerman |
| 5,633,504 A | 5/1997 | Collins et al. |
| 5,665,822 A | 9/1997 | Bitler et al. |
| 5,674,282 A | 10/1997 | Cumming |
| 5,676,669 A | 10/1997 | Colvard |
| 5,693,095 A | 12/1997 | Freeman et al. |
| 5,697,973 A | 12/1997 | Peyman et al. |
| 5,702,441 A | 12/1997 | Zhou |
| 5,774,273 A | 6/1998 | Bornhorst |
| 5,776,191 A | 7/1998 | Mazzocco |
| 5,776,192 A | 7/1998 | Mcdonald |
| 5,800,533 A | 9/1998 | Eggleston et al. |
| 5,843,188 A | 12/1998 | Mcdonald |
| 5,891,931 A | 4/1999 | Leboeuf et al. |
| 5,928,282 A | 7/1999 | Nigam |
| 5,964,802 A | 10/1999 | Anello et al. |
| 5,968,095 A | 10/1999 | Norrby |
| 5,984,962 A | 11/1999 | Anello et al. |
| 6,013,101 A | 1/2000 | Israel |
| 6,015,842 A | 1/2000 | Leboeuf et al. |
| 6,102,539 A | 8/2000 | Tucker |
| 6,117,171 A | 9/2000 | Skottun |
| 6,124,980 A | 9/2000 | Cerbell |
| 6,139,576 A | 10/2000 | Doyle et al. |
| 6,160,084 A | 12/2000 | Langer et al. |
| 6,176,878 B1 | 1/2001 | Gwon et al. |
| 6,180,687 B1 | 1/2001 | Hammer et al. |
| 6,188,526 B1 | 2/2001 | Sasaya et al. |
| 6,190,410 B1 | 2/2001 | Lamielle et al. |
| 6,195,807 B1 | 3/2001 | Chou |
| 6,197,059 B1 | 3/2001 | Cumming |
| 6,217,612 B1 | 4/2001 | Woods |
| 6,225,367 B1 | 5/2001 | Chaouk et al. |
| 6,229,641 B1 | 5/2001 | Kosaka |
| 6,299,641 B1 | 10/2001 | Woods |
| 6,302,911 B1 | 10/2001 | Hanna |
| 6,322,589 B1 | 11/2001 | Cumming |
| 6,342,073 B1 | 1/2002 | Cumming et al. |
| 6,348,437 B1 | 2/2002 | Avery et al. |
| 6,387,126 B1 | 5/2002 | Cumming |
| 6,388,043 B1 | 5/2002 | Langer et al. |
| 6,406,494 B1 | 6/2002 | Laguette et al. |
| 6,413,262 B2 | 7/2002 | Saishin et al. |
| 6,423,094 B1 | 7/2002 | Sarfarazi |
| 6,436,092 B1 | 8/2002 | Peyman |
| 6,443,985 B1 | 9/2002 | Woods |
| 6,450,642 B1 | 9/2002 | Jethmalani et al. |
| 6,464,725 B2 | 10/2002 | Skotton |
| 6,488,708 B2 | 12/2002 | Sarfarazi |
| 6,493,151 B2 | 12/2002 | Schachar |
| 6,503,276 B2 | 1/2003 | Lang et al. |
| 6,517,577 B1 | 2/2003 | Callahan et al. |

(56) References Cited

U.S. PATENT DOCUMENTS

| | | |
|---|---|---|
| 6,528,602 B1 | 3/2003 | Freeman et al. |
| 6,551,354 B1 | 4/2003 | Ghazizadeh et al. |
| 6,552,860 B1 | 4/2003 | Alden |
| 6,554,859 B1 | 4/2003 | Lang et al. |
| 6,585,768 B2 | 7/2003 | Hamano et al. |
| 6,589,550 B1 | 7/2003 | Hodd et al. |
| 6,592,621 B1 | 7/2003 | Domino |
| 6,599,317 B1 | 7/2003 | Weinschenk et al. |
| 6,601,956 B1 | 8/2003 | Jean et al. |
| 6,610,350 B2 | 8/2003 | Suzuki et al. |
| 6,616,691 B1 | 9/2003 | Tran |
| 6,616,692 B1 | 9/2003 | Glick et al. |
| 6,638,304 B2 | 10/2003 | Azar |
| 6,638,305 B2 | 10/2003 | Laguette |
| 6,638,306 B2 | 10/2003 | Cumming |
| 6,645,245 B1 | 11/2003 | Preussner |
| 6,645,246 B1 | 11/2003 | Weinschenk et al. |
| 6,656,223 B2 | 12/2003 | Brady |
| 6,660,035 B1 | 12/2003 | Lang et al. |
| 6,692,525 B2 | 2/2004 | Brady et al. |
| 6,695,881 B2 | 2/2004 | Peng et al. |
| 6,709,108 B2 | 3/2004 | Levine et al. |
| 6,712,848 B1 | 3/2004 | Wolf et al. |
| 6,730,123 B1 | 5/2004 | Klopotek |
| 6,743,388 B2 | 6/2004 | Sridharan et al. |
| 6,749,632 B2 | 6/2004 | Sandstedt et al. |
| 6,749,634 B2 | 6/2004 | Hanna |
| 6,786,934 B2 | 9/2004 | Zadno-Azizi et al. |
| 6,818,158 B2 | 11/2004 | Pham et al. |
| 6,827,738 B2 | 12/2004 | Willis et al. |
| 6,836,374 B2 | 12/2004 | Esch et al. |
| 6,860,601 B2 | 3/2005 | Shadduck |
| 6,878,320 B1 | 4/2005 | Alderson et al. |
| 6,884,261 B2 | 4/2005 | Zadno-Azizi et al. |
| 6,899,732 B2 | 5/2005 | Zadno-Azizi et al. |
| 6,899,850 B2 | 5/2005 | Haywood et al. |
| 6,914,247 B2 | 7/2005 | Duggan et al. |
| 6,926,736 B2 | 8/2005 | Peng et al. |
| 6,935,743 B2 | 8/2005 | Shadduck |
| 6,949,093 B1 | 9/2005 | Peyman |
| 6,966,649 B2 | 11/2005 | Shadduck |
| 6,969,403 B2 | 11/2005 | Peng et al. |
| 7,001,374 B2 | 2/2006 | Peyman |
| 7,060,094 B2 | 6/2006 | Shahinpoor et al. |
| 7,068,439 B2 | 6/2006 | Esch et al. |
| 7,070,276 B2 | 7/2006 | Koretz |
| 7,074,227 B2 | 7/2006 | Portney |
| 7,122,053 B2 | 10/2006 | Esch |
| 7,144,423 B2 | 12/2006 | Mcdonald |
| 7,163,543 B2 | 1/2007 | Smedley et al. |
| 7,217,288 B2 | 5/2007 | Esch et al. |
| 7,241,312 B2 | 7/2007 | Lai et al. |
| 7,247,168 B2 | 7/2007 | Esch et al. |
| 7,261,737 B2 | 8/2007 | Esch et al. |
| 7,264,351 B2 | 9/2007 | Shadduck |
| 7,276,619 B2 | 10/2007 | Kunzler et al. |
| 7,278,739 B2 | 10/2007 | Shadduck |
| 7,311,194 B2 | 12/2007 | Jin et al. |
| 7,438,723 B2 | 10/2008 | Esch |
| 7,485,144 B2 | 2/2009 | Esch |
| 7,494,505 B2 | 2/2009 | Kappelhof et al. |
| 7,637,947 B2 | 12/2009 | Smith et al. |
| 7,763,069 B2 | 7/2010 | Brady et al. |
| 7,776,088 B2 | 8/2010 | Shadduck |
| 7,988,292 B2 | 8/2011 | Neal et al. |
| 8,048,155 B2 | 11/2011 | Shadduck |
| 8,158,712 B2 | 4/2012 | Your |
| 8,162,927 B2 | 4/2012 | Peyman |
| 8,303,656 B2 | 11/2012 | Shadduck |
| 8,314,927 B2 | 11/2012 | Choi et al. |
| 8,328,869 B2 | 12/2012 | Smiley et al. |
| 8,361,145 B2 | 1/2013 | Scholl et al. |
| 8,425,599 B2 | 4/2013 | Shadduck |
| 8,447,086 B2 | 5/2013 | Hildebrand et al. |
| 8,454,688 B2 | 6/2013 | Esch et al. |
| 8,668,734 B2 | 3/2014 | Hildebrand et al. |
| 8,900,298 B2 | 12/2014 | Anvar et al. |
| 8,956,408 B2 | 2/2015 | Smiley et al. |
| 8,968,396 B2 | 3/2015 | Matthews et al. |
| 8,992,609 B2 | 3/2015 | Shadduck |
| 9,044,317 B2 | 6/2015 | Hildebrand et al. |
| 9,277,987 B2 | 3/2016 | Smiley et al. |
| 9,456,895 B2 | 10/2016 | Shadduck |
| 9,693,858 B2 | 7/2017 | Hildebrand et al. |
| 9,855,139 B2 | 1/2018 | Matthews et al. |
| 10,159,566 B2 | 12/2018 | Hadba et al. |
| 10,195,020 B2 | 2/2019 | Matthews |
| 10,299,913 B2 | 5/2019 | Smiley et al. |
| 10,350,060 B2 | 7/2019 | Smiley et al. |
| 10,433,949 B2 | 10/2019 | Smiley et al. |
| 10,433,950 B2 | 10/2019 | Shadduck |
| 10,534,113 B2 | 1/2020 | Shadduck |
| 10,595,989 B2 | 3/2020 | Hildebrand et al. |
| 11,471,272 B2 * | 10/2022 | Smiley ................ A61L 27/443 |
| 11,660,182 B2 * | 5/2023 | Smiley ................ A61L 27/50 623/6.13 |
| 12,167,959 B2 | 12/2024 | Smiley et al. |
| 12,245,930 B2 | 3/2025 | Bor |
| 2001/0001836 A1 | 5/2001 | Cumming |
| 2001/0016771 A1 | 8/2001 | Cumming |
| 2001/0039449 A1 | 11/2001 | Johnson et al. |
| 2001/0051826 A1 | 12/2001 | Bogaert et al. |
| 2002/0016629 A1 | 2/2002 | Sandstedt et al. |
| 2002/0046783 A1 | 4/2002 | Johnson et al. |
| 2002/0055777 A1 | 5/2002 | Cumming et al. |
| 2002/0072795 A1 | 6/2002 | Green |
| 2002/0095212 A1 | 7/2002 | Boehm |
| 2002/0107568 A1 | 8/2002 | Zadno-Azizi et al. |
| 2002/0111678 A1 | 8/2002 | Zadno-Azizi et al. |
| 2002/0116057 A1 | 8/2002 | Ting et al. |
| 2002/0116058 A1 | 8/2002 | Zadno-Azizi et al. |
| 2002/0116059 A1 | 8/2002 | Zadno-Azizi et al. |
| 2002/0116060 A1 | 8/2002 | Nguyen et al. |
| 2002/0116061 A1 | 8/2002 | Zadno-Azizi et al. |
| 2002/0133228 A1 | 9/2002 | Sarver |
| 2002/0161434 A1 | 10/2002 | Laguette et al. |
| 2002/0161435 A1 | 10/2002 | Portney |
| 2002/0177896 A1 | 11/2002 | Israel |
| 2002/0188351 A1 | 12/2002 | Laguette |
| 2002/0193876 A1 | 12/2002 | Lang et al. |
| 2003/0003295 A1 | 1/2003 | Dreher et al. |
| 2003/0004569 A1 | 1/2003 | Haefliger |
| 2003/0018384 A1 | 1/2003 | Valyunin et al. |
| 2003/0042176 A1 | 3/2003 | Alderson et al. |
| 2003/0050695 A1 | 3/2003 | Lin et al. |
| 2003/0050696 A1 | 3/2003 | Cumming |
| 2003/0060878 A1 | 3/2003 | Shadduck |
| 2003/0060881 A1 | 3/2003 | Glick et al. |
| 2003/0078656 A1 | 4/2003 | Nguyen |
| 2003/0078657 A1 | 4/2003 | Zadno-Azizi et al. |
| 2003/0078658 A1 | 4/2003 | Zadno-Azizi |
| 2003/0083744 A1 | 5/2003 | Khoury |
| 2003/0109925 A1 | 6/2003 | Ghazizadeh et al. |
| 2003/0109926 A1 | 6/2003 | Portney |
| 2003/0130732 A1 | 7/2003 | Sarfarazi |
| 2003/0135272 A1 | 7/2003 | Brady et al. |
| 2003/0149480 A1 | 8/2003 | Shadduck |
| 2003/0158599 A1 | 8/2003 | Brady et al. |
| 2003/0171808 A1 | 9/2003 | Phillips |
| 2003/0183960 A1 | 10/2003 | Buazza et al. |
| 2003/0187505 A1 | 10/2003 | Liao |
| 2003/0199977 A1 | 10/2003 | Cumming |
| 2003/0236376 A1 | 12/2003 | Kindt-Larsen et al. |
| 2004/0001180 A1 | 1/2004 | Epstein |
| 2004/0006386 A1 | 1/2004 | Valint et al. |
| 2004/0006387 A1 | 1/2004 | Kelman |
| 2004/0008419 A1 | 1/2004 | Schachar |
| 2004/0015236 A1 | 1/2004 | Sarfarazi |
| 2004/0039446 A1 | 2/2004 | Mcnicholas |
| 2004/0054408 A1 | 3/2004 | Glick et al. |
| 2004/0059343 A1 | 3/2004 | Shearer et al. |
| 2004/0066489 A1 | 4/2004 | Benedikt et al. |
| 2004/0082993 A1 | 4/2004 | Woods |
| 2004/0082994 A1 | 4/2004 | Woods et al. |

(56) References Cited

U.S. PATENT DOCUMENTS

| | | |
|---|---|---|
| 2004/0085511 A1 | 5/2004 | Uno et al. |
| 2004/0085515 A1 | 5/2004 | Roffman et al. |
| 2004/0088050 A1 | 5/2004 | Norrby et al. |
| 2004/0111151 A1 | 6/2004 | Paul et al. |
| 2004/0111152 A1 | 6/2004 | Kelman |
| 2004/0111153 A1 | 6/2004 | Woods et al. |
| 2004/0127984 A1 | 7/2004 | Paul et al. |
| 2004/0162612 A1 | 8/2004 | Portney et al. |
| 2004/0169932 A1 | 9/2004 | Esch et al. |
| 2004/0181279 A1 | 9/2004 | Nun |
| 2004/0184158 A1 | 9/2004 | Shadduck |
| 2004/0190153 A1 | 9/2004 | Esch |
| 2004/0230203 A1 | 11/2004 | Yaguchi |
| 2005/0021139 A1 | 1/2005 | Shadduck |
| 2005/0090612 A1 | 4/2005 | Soane et al. |
| 2005/0113911 A1 | 5/2005 | Peyman |
| 2005/0119740 A1 | 6/2005 | Esch et al. |
| 2005/0125000 A1 | 6/2005 | Tourrette et al. |
| 2005/0131535 A1 | 6/2005 | Woods |
| 2005/0146685 A1 | 7/2005 | Hanaki et al. |
| 2005/0149183 A1 | 7/2005 | Shadduck |
| 2005/0165410 A1 | 7/2005 | Zadno-Azizi et al. |
| 2005/0251253 A1 | 11/2005 | Gross |
| 2005/0264756 A1 | 12/2005 | Esch |
| 2006/0021623 A1 | 2/2006 | Miller et al. |
| 2006/0041307 A1 | 2/2006 | Esch et al. |
| 2006/0061729 A1 | 3/2006 | Shadduck |
| 2006/0069433 A1 | 3/2006 | Nun |
| 2006/0084949 A1 | 4/2006 | Peyman |
| 2006/0158611 A1 | 7/2006 | Piers et al. |
| 2006/0246112 A1 | 11/2006 | Snyder et al. |
| 2006/0253196 A1 | 11/2006 | Woods |
| 2007/0010827 A1 | 1/2007 | Tu et al. |
| 2007/0010880 A1 | 1/2007 | Esch |
| 2007/0027452 A1 | 2/2007 | Varner et al. |
| 2007/0088433 A1 | 4/2007 | Esch et al. |
| 2007/0100445 A1 | 5/2007 | Shadduck |
| 2007/0106377 A1 | 5/2007 | Smith et al. |
| 2007/0156236 A1 | 7/2007 | Stenger |
| 2007/0162112 A1 | 7/2007 | Burriesci et al. |
| 2007/0203578 A1 | 8/2007 | Scholl et al. |
| 2007/0213817 A1 | 9/2007 | Esch et al. |
| 2007/0260308 A1 | 11/2007 | Tran |
| 2007/0299487 A1 | 12/2007 | Shadduck |
| 2008/0015689 A1 | 1/2008 | Esch et al. |
| 2008/0046074 A1 | 2/2008 | Smith et al. |
| 2008/0046075 A1 | 2/2008 | Esch et al. |
| 2008/0195027 A1 | 8/2008 | Coroneo |
| 2008/0306587 A1 | 12/2008 | Your |
| 2009/0005865 A1* | 1/2009 | Smiley .................. A61F 2/1635 623/6.13 |
| 2009/0030425 A1 | 1/2009 | Smiley et al. |
| 2009/0069786 A1 | 3/2009 | Vesely et al. |
| 2009/0079940 A1 | 3/2009 | Dai et al. |
| 2009/0149952 A1 | 6/2009 | Shadduck |
| 2009/0155371 A1 | 6/2009 | Sojka et al. |
| 2009/0312836 A1 | 12/2009 | Pinchuk et al. |
| 2010/0016965 A1 | 1/2010 | Hong et al. |
| 2010/0131058 A1 | 5/2010 | Shadduck |
| 2010/0179653 A1 | 7/2010 | Argento et al. |
| 2010/0228344 A1 | 9/2010 | Shadduck |
| 2010/0228346 A1 | 9/2010 | Esch |
| 2010/0324671 A1 | 12/2010 | Shadduck |
| 2010/0324672 A1 | 12/2010 | Esch et al. |
| 2011/0052020 A1 | 3/2011 | Hildebrand et al. |
| 2011/0208301 A1 | 8/2011 | Anvar et al. |
| 2011/0282442 A1 | 11/2011 | Scholl et al. |
| 2011/0282443 A1 | 11/2011 | Smiley et al. |
| 2011/0288638 A1 | 11/2011 | Smiley et al. |
| 2012/0022547 A1 | 1/2012 | Hildebrand et al. |
| 2012/0078361 A1 | 3/2012 | Shadduck |
| 2012/0226351 A1 | 9/2012 | Peyman |
| 2012/0245591 A1 | 9/2012 | Matthews |
| 2013/0060331 A1 | 3/2013 | Shadduck |
| 2013/0103145 A1 | 4/2013 | John et al. |
| 2013/0103146 A1 | 4/2013 | Smiley et al. |
| 2013/0131794 A1 | 5/2013 | Smiley et al. |
| 2013/0250239 A1 | 9/2013 | Hildebrand et al. |
| 2013/0268070 A1 | 10/2013 | Esch et al. |
| 2014/0031737 A1 | 1/2014 | Silvestrini |
| 2014/0249625 A1 | 9/2014 | Shadduck |
| 2015/0057642 A1 | 2/2015 | Zickler et al. |
| 2015/0087743 A1 | 3/2015 | Anvar et al. |
| 2015/0126809 A1 | 5/2015 | Silvestrini et al. |
| 2015/0202041 A1 | 7/2015 | Shadduck |
| 2015/0238310 A1 | 8/2015 | Matthews et al. |
| 2015/0257874 A1 | 9/2015 | Hildebrand et al. |
| 2016/0038278 A1 | 2/2016 | Matthews |
| 2016/0184091 A1 | 6/2016 | Smiley et al. |
| 2016/0184092 A1 | 6/2016 | Smiley et al. |
| 2016/0262875 A1 | 9/2016 | Smith et al. |
| 2017/0020662 A1 | 1/2017 | Shadduck |
| 2017/0049561 A1 | 2/2017 | Smiley et al. |
| 2017/0079773 A1 | 3/2017 | Matthews et al. |
| 2017/0281334 A1 | 10/2017 | Zhao |
| 2017/0290658 A1 | 10/2017 | Hildebrand et al. |
| 2018/0085213 A1* | 3/2018 | Hadba .................. A61F 2/1659 |
| 2018/0125640 A1 | 5/2018 | Smiley et al. |
| 2018/0132997 A1 | 5/2018 | Smiley et al. |
| 2018/0147051 A1 | 5/2018 | Scholl et al. |
| 2018/0153682 A1 | 6/2018 | Hajela et al. |
| 2018/0177589 A1 | 6/2018 | Argento et al. |
| 2018/0200112 A1 | 7/2018 | Krampert et al. |
| 2018/0256315 A1 | 9/2018 | Hildebrand et al. |
| 2019/0053892 A1 | 2/2019 | Siney et al. |
| 2019/0076243 A1 | 3/2019 | Hadba et al. |
| 2019/0361231 A1 | 11/2019 | Kurz |
| 2019/0374333 A1 | 12/2019 | Shadduck |
| 2020/0315848 A1 | 10/2020 | Rosen |
| 2020/0332085 A1 | 10/2020 | Ebe et al. |
| 2020/0337833 A1 | 10/2020 | Green |
| 2020/0405541 A1 | 12/2020 | Raksi |
| 2021/0100649 A1 | 4/2021 | Smiley |
| 2021/0100650 A1 | 4/2021 | Smiley et al. |
| 2021/0186320 A1 | 6/2021 | Copland |
| 2022/0409363 A1 | 12/2022 | Smiley |
| 2023/0191730 A1 | 6/2023 | Walz et al. |
| 2023/0240836 A1 | 8/2023 | Irby et al. |
| 2023/0248509 A1 | 8/2023 | Smiley et al. |
| 2024/0148554 A1 | 5/2024 | Paliwal et al. |
| 2024/0325139 A1 | 10/2024 | Walz et al. |
| 2025/0000642 A1 | 1/2025 | Bor |
| 2025/0057644 A1 | 2/2025 | Smiley et al. |

FOREIGN PATENT DOCUMENTS

| | | |
|---|---|---|
| CN | 1378440 | 11/2002 |
| CN | 1384727 | 12/2002 |
| EP | 0898972 | 3/1999 |
| FR | 2655841 | 6/1991 |
| FR | 2784575 | 12/2000 |
| JP | H05(1993)-171056 | 7/1993 |
| JP | 07-044938 | 5/1995 |
| JP | 08-501715 | 2/1996 |
| JP | 08-224295 | 9/1996 |
| JP | 09-294754 | 11/1997 |
| JP | 10-206609 | 8/1998 |
| JP | 11-047168 | 2/1999 |
| JP | 1999-047168 | 2/1999 |
| JP | 11-056998 | 3/1999 |
| JP | 11-169391 | 6/1999 |
| JP | 11-276509 | 10/1999 |
| JP | 11-332903 | 12/1999 |
| JP | 11-47168 | 9/2000 |
| JP | 2000-250203 | 9/2000 |
| JP | 2001-502592 | 2/2001 |
| JP | 2003-144387 | 5/2003 |
| JP | 2003-524503 | 8/2003 |
| JP | 2003-530978 | 10/2003 |
| JP | 2006-523130 | 10/2006 |
| JP | 2007-513715 | 5/2007 |
| JP | 2007-516794 | 6/2007 |
| JP | 2007-518447 | 7/2007 |
| JP | 2010-095719 | 4/2010 |

(56) References Cited

FOREIGN PATENT DOCUMENTS

| | | |
|---|---|---|
| JP | 2010-534520 | 11/2010 |
| JP | 2016-138050 | 8/2016 |
| JP | 2017-148614 | 8/2017 |
| JP | 2018-047096 | 3/2018 |
| SU | 1810052 | 4/1993 |
| WO | WO 1995/002378 | 1/1995 |
| WO | WO 1997/006751 | 2/1997 |
| WO | WO 2000/041650 | 7/2000 |
| WO | WO 2000/064655 | 11/2000 |
| WO | WO 2001/060286 | 8/2001 |
| WO | WO 2001/089435 | 11/2001 |
| WO | WO 2001/097742 | 12/2001 |
| WO | WO 2002/051338 | 7/2002 |
| WO | WO 2004/010895 | 2/2004 |
| WO | WO 2004/046768 | 6/2004 |
| WO | WO 2004/072689 | 8/2004 |
| WO | WO 2004/081613 | 9/2004 |
| WO | WO 2005/018504 | 3/2005 |
| WO | WO 2005/084588 | 9/2005 |
| WO | WO 2009/015234 | 1/2009 |
| WO | WO 2018/222558 | 12/2018 |
| WO | WO 2018/227014 | 12/2018 |
| WO | WO 2021/067574 | 4/2021 |
| WO | WO 2021/067579 | 4/2021 |
| WO | WO 2022/216451 | 10/2022 |
| WO | WO 2023/122490 | 6/2023 |
| WO | WO 2023/147224 | 8/2023 |
| WO | WO 2024/102536 | 5/2024 |
| WO | WO 2024/206251 | 10/2024 |
| WO | WO 2025/006182 | 1/2025 |

OTHER PUBLICATIONS

Baughman, "Avoiding the shrink," Nature, vol. 425, pp. 667, Oct. 16, 2003.
Conlisk, A. T. et al. "Mass Transfer and Flow in Electrically Charged Micro- and Nano-channels," Analytical Chemistry, vol. 74; iss. 9; pp. 2139-2150; May 2002.
Dubbelman et al. "The Thickness of the Aging Human Lens Obtained from Corrected Scheimpflug Images," Optometry & Vision Science; vo. 78; iss. 6; pp. 411-416; Jun. 2001.
Gorder, P. F.; Electricity can pump medicine in implanted medical devices; Ohio State Research News; 3 pgs.; May 2, 2002 (printed from internet Aug. 19, 2010).
Gordon, "Applications of shape memory polyurethanes," Proceedings of the First Intl Conf. on Shape Memory and Superelastic Tech., Asilomar Conference Center, Pacific Grove, CA, USA, pp. 115-120, Mar. 1994.
Gruber et al. "Exhaustive soxhlet extraction for the complete removal of residual compounds," Journal of Biomedical Materials Research, vol. 53; No. 5; pp. 445-448; Mar. 2000.
Jeon et al., "Shape memory and nanostructure in poly(norbornyl-POSS) copolymers," Polymer International, vol. 49, pp. 453-457, May 2000.
Kim et al., "Polyurethanes having shape memory effects," Polymer, vol. 37, No. 26, pp. 5781-5793, Dec. 1996.
Lakes et al., "Dramatically stiffer elastic composite materials due to negative stiffness phase?," Journal of the Mechanics and Physics of Solids, vol. 50, pp. 979-1009, May 2002.
Lakes et al., "Extreme damping in composite materials with negative-stiffness inclusions," Nature, vol. 410, pp. 565-567, Mar. 29, 2001.
Lakes et al., "Microbuckling instability in elastomeric cellular sollids," J. Materials Science, vol. 28, pp. 4667-4672, Jan. 1993.
Lakes, "A broader view of membranes," Nature, vol. 414, pp. 503-504, Nov. 29, 2001.
Lakes, "Deformations in extreme matter," Science; perspectives; vol. 288; No. 5473; pp. 1976-1977; Jun. 16, 2000.
Lakes, "Extreme damping in compliant composites with a negative-stiffness phase," Philosophical Magazine Letters, vol. 81, No. 2, pp. 95-100, Feb. 2001.
Lakes, "Extreme damping in composite materials with a negative stiffness phase," Physical Review Letters, vol. 86, No. 13, pp. 2897-2900, Mar. 26, 2001.
Lakes, "Negative poisson's ratio materials," Science, vol. 238, pp. 551, Oct. 23, 1987.
Lakes, "No contractile obligations," Nature, vol. 358, pp. 713-714, Dec. 31, 1992.
Lendlein et al., "Biodegradable, elastic shape-memory polymers for potential biomedical applications", Science; vol. 296; pp. 1673-1676; May 31, 2002.
Lendlein et al., "Shape-memory polymers," Angew. Chem. Int. Ed.; vol. 41; pp. 2034-2057; Jun. 2002.
Li et al., "Crystallinity and morphology of segmented polyurethanes with different soft-segment length," Journal of Applied Polymer Science, vol. 62, pp. 631-638, Oct. 1996.
Liu et al., "Thermomechanical characterization of a tailored series of shape memory polymers," Journal of Applied Medical Polymers, vol. 6, No. 2, Dec. 2002.
Mather et al., "Strain recovery in POSS hybrid thermoplastics," Polymer Preprints, vol. 41, No. 1, pp. 528-529, Feb. 2000.
Metcalfe et al., "Cold hibernated elastic memory foams for endovascular interventions," Biomaterials, vol. 24, pp. 491-497, Feb. 2003.
Takahashi et al., "Structure and properties of shape-memory polyurethane block copolymers," Journal of Applied Polymer Science, vol. 60, pp. 1061-1069, May 1996.
Tehrani et al. "Capsule measuring ring to predict capsular bag diameter and follow its course after foldable intraocular lens implantation," J Cataract Refract Surg.; vol. 29; No. 11; pp. 2127-2134; Nov. 29, 2003.
Tobushi et al., "Thermomechanical properties of shape memory polymers of polyurethane series and their applications," Journal de Physique IV, Colloque C1, vol. 6, pp. 377-384, Aug. 1996.
Vass et al. "Prediction of pseudophakic capsular bag diameter based on biometric variables," J Cataract Refract Surg.; vol. 25; pp. 1376-1381; Oct. 1999.
Wang et al., "Deformation of extreme viscoelastic metals and composites," Materials Science and Engineerring A, vol. 370, pp. 41-49, Apr. 15, 2004.
Wang et al., "Extreme stiffness systems due to negative stiffness elements," American Journal of Physics, vol. 72, No. 1, pp. 40-50, Jan. 2004.
Wyant et al; "Basic Wavefront Aberration Theory for Optical Metrology," Applied Optics and Optical Engineering, vol. XI, pp. 1, 28-39, Aug. 10, 1992.
Xu et al., "Making negative poisson's ratio microstructures by soft lithography," Advanced Materials, vol. 11, No. 14, pp. 1186-1189, Jun. 1999.
U.S. Appl. No. 15/284,350, filed Oct. 3, 2016.
U.S. Appl. No. 16/549,772, filed Aug. 23, 2019.
U.S. Appl. No. 10/795,166, filed Mar. 6, 2004.
U.S. Appl. No. 11/214,538, filed Aug. 29, 2005.
U.S. Appl. No. 11/849,921, filed Sep. 4, 2007.
U.S. Appl. No. 13/669,251, filed Nov. 5, 2012.
U.S. Appl. No. 17/060,901, filed Oct. 1, 2020.
U.S. Appl. No. 17/060,940, filed Oct. 1, 2020.
U.S. Appl. No. 17/655,768, filed Mar. 21, 2022.
Sun, M. et al. "Intraocular lens alignment from an en face optical coherence tomography image Purkinje-like method", Optical Engineering, Society of Photo-Optical Instrumentation Engineers, vol. 51, No. 6, pp. 061704-1 to 061704-9, Jun. 1, 2014.

* cited by examiner

ADJUSTABLE INTRAOCULAR LENSES AND METHODS OF POST-OPERATIVELY ADJUSTING INTRAOCULAR LENSES

CROSS-REFERENCE TO RELATED APPLICATION

This application is a continuation of U.S. patent application Ser. No. 17/060,940 filed on Oct. 1, 2020, which claims the benefit of U.S. Provisional Application No. 62/911,039 filed on Oct. 4, 2019, the contents of which are incorporated herein by reference in their entireties.

TECHNICAL FIELD

The present disclosure relates generally to the field of intraocular lenses, and, more specifically, to adjustable intraocular lenses and methods of adjusting intraocular lenses post-operatively.

BACKGROUND

A cataract is a condition involving the clouding over of the normally clear lens of a patient's eye. Cataracts occur as a result of aging, hereditary factors, trauma, inflammation, metabolic disorders, or exposure to radiation. Age-related cataract is the most common type of cataracts. In treating a cataract, the surgeon removes the crystalline lens matrix from the patient's lens capsule and replaces it with an intraocular lens (IOL).

However, current IOL surgery may leave some patients unsatisfied with their refractive outcomes. In some cases, the pre-operative biometry measurements made on a patient's eye may be incorrect, leading to IOLs with the wrong lens power being prescribed and implanted within the patient. In other cases, once an IOL is implanted within the capsular bag, an aggressive healing response by tissue within the capsular bag can affect the optical power of the IOL. Moreover, a patient's cornea or muscles within the eye may change as a result of injury, disease, or aging. In such cases, it may also be necessary to adjust the patient's implanted IOLs to account for such changes.

Therefore, a solution is needed which allows for post-implant adjustment of IOLs to address the aforementioned problems without having to undergo additional surgery. Such a solution should not be overly complicated and still allow the IOLs to be cost-effectively manufactured.

SUMMARY

Disclosed herein are adjustable intraocular lenses and methods of adjusting intraocular lenses post-operatively. Such adjustable intraocular lenses can also be referred to as adjustable static-focus intraocular lenses or non-accommodating fluid-adjustable intraocular lenses.

In one embodiment, an intraocular lens is disclosed comprising an optic portion and a peripheral portion coupled to the optic portion. The peripheral portion can comprise a composite material comprising an energy absorbing constituent and a plurality of expandable components. A base power of the optic portion can be configured to change in response to an external energy directed at the composite material. The base power of the optic portion can be configured to be unresponsive to forces applied to the peripheral portion by a capsular bag when the intraocular lens is implanted within the capsular bag.

In some embodiments, the expandable components can be expandable microspheres. Each of the expandable microspheres can comprise a blowing agent contained within a thermoplastic shell. A thickness of the thermoplastic shell can be configured to change in response to the external energy directed at the composite material.

In certain embodiments, the blowing agent can be a branched-chain hydrocarbon. For example, the branched-chain hydrocarbon can be isopentane. Also, for example, the thermoplastic shell can be made in part of an acrylonitrile copolymer.

In some embodiments, the diameter of at least one of the expandable microspheres can be configured to increase between about 2× to about 4× in response to the external energy directed at the composite material. A volume of at least one of the expandable components can be configured to expand between about 10× to 50× in response to the external energy directed at the composite material.

In some embodiments, the expandable components can comprise between about 5% to about 15% by weight of the composite material. For example, the expandable components comprise about 10% by weight of the composite material.

In some embodiments, the energy absorbing constituent can be an energy absorbing colorant. A color of the energy absorbing colorant can be visually perceptible when the intraocular lens is implanted within the eye.

In some embodiments, the energy absorbing colorant can be a dye. For example, the dye can be an azo dye. As a more specific example, the dye can be a Disperse Red 1 dye.

In some embodiments, the energy absorbing colorant can be an energy absorbing pigment. For example, the energy absorbing pigment can be graphitized carbon black. In certain embodiments, the energy absorbing constituent can comprise between about 0.025% to about 1.00% by weight of the composite material.

In some embodiments, the peripheral portion can be made in part of a cross-linked copolymer comprising a copolymer blend. In these embodiments, the composite material can also be made in part of the copolymer blend.

The composite material can be cured to the cross-linked copolymer at a location within the peripheral portion. The composite material can remain substantially fixed at the location.

The base power of the optic portion can be configured to change between about ±0.05 D to about ±0.5 D in response to pulses of the external energy directed at the composite material. For example, the base power of the optic portion can be configured to change by about 0.1 D in response to the pulses of the external energy directed at the composite material.

The base power of the optic portion can be configured to change in total between about ±1.0 D and about ±2.0 D. The change in the base power can be a persistent change.

In some embodiments, the external energy can be light energy. In these embodiments, the light energy can be a laser light. The laser light can have a wavelength of between about 488 nm to about 650 nm. For example, the laser light can be a green laser light. The green laser light can have a wavelength of about 532 nm.

In other embodiments, the laser light can have a wavelength of between about 946 nm to about 1120 nm. For example, the laser light can have a wavelength of about 1030 nm. Also, for example, the laser light can have a wavelength of about 1064 nm.

In some embodiments, the laser light can be emitted by a neodymium-doped yttrium aluminum garnet (Nd:YAG) laser. In other embodiments, the laser light can be emitted by a femtosecond laser.

The energy absorbing constituent can be configured to transfer thermal energy to the plurality of expandable components in response to the external energy directed at the composite material.

In some embodiments, the composite material can be formed as discrete peripheral components such that directing the external energy at one discrete peripheral component causes a change in the base power of the optic portion and directing the external energy at another discrete peripheral component also causes a change in the base power of the optic portion. In certain embodiments, the peripheral portion can comprise between 20 and 40 peripheral components.

The optic portion of the IOL can comprise an optic fluid chamber and the peripheral portion can comprise at least one peripheral fluid chamber in fluid communication with the optic fluid chamber. In some embodiments, the peripheral fluid chamber is curved and the peripheral fluid chamber follows a curvature of the optic portion.

The peripheral fluid chamber can have a chamber height. The chamber height can be between about 0.1 mm to about 0.3 mm.

In some embodiments, the composite material can be configured as a chamber expander. The chamber expander can be configured to expand in response to the external energy directed at the chamber expander. Expansion of the chamber expander can increase a volume of the peripheral fluid chamber. The base power of the optic portion can be configured to decrease in response to the external energy directed at the chamber expander. The chamber expander can be configured as an expandable column extending from a chamber anterior wall to a chamber posterior wall.

In some embodiments, the composite material can be configured as a space-filler or piston. The space-filler or piston can be configured to expand in response to the external energy directed at the space-filler or piston. Expansion of the space-filler or piston can decrease a volume of the peripheral fluid chamber. The space-filler or piston can be configured as a pad extending from either a chamber anterior wall or a chamber posterior wall. The base power of the optic portion can be configured to increase in response to the external energy directed at the space-filler or piston.

The base power can be configured to change in response to fluid displacement between the optic fluid chamber and the peripheral fluid chamber as a result of the external energy directed at the composite material.

In certain embodiments, the peripheral portion can comprise a first composite material and a second composite material. In these embodiments, the first composite material can comprise a first energy absorbing constituent and the second composite material can comprise a second energy absorbing constituent. A color of the first energy absorbing constituent can be different from a color of the second energy absorbing constituent.

In some embodiments, the peripheral portion can be configured as at least one haptic and the peripheral fluid chamber can be defined within the haptic. In these embodiments, the peripheral fluid chamber can extend only partially into the haptic.

The haptic can comprise a haptic proximal portion and a haptic distal portion. The haptic distal portion can comprise a haptic distal arm unattached to the optic portion except via the haptic proximal portion.

In some embodiments, the haptic distal arm can comprise a kink or bend.

The peripheral fluid chamber can be defined within the haptic proximal portion and a chamber segment of the haptic proximal portion can be unconnected to or separated from the optic portion by a gap or space. The haptic can be connected to the optic portion at a proximal end of the haptic and at a distal connecting portion located distally of the chamber segment.

In some embodiments, the proximal end of the haptic can be connected to and extend from a lateral side of the optic portion. In these embodiments, the lateral side can have a side height of about 0.65 mm.

The peripheral portion can be configured as a first haptic comprising a first haptic fluid chamber and a second haptic comprising a second haptic fluid chamber. The optic portion can comprise an optic fluid chamber.

The first haptic fluid chamber can be in fluid communication with the optic fluid chamber via a first fluid channel. The second haptic fluid chamber can be in fluid communication with the optic fluid chamber via a second fluid channel. The first fluid channel can be positioned diametrically opposed to the second fluid channel.

In some embodiments, the optic fluid chamber, the first haptic fluid chamber, and the second haptic fluid chamber can comprise a fluid having a total fluid volume of between about 10 µL and about 20 µL. Each of the first haptic fluid chamber and the second haptic fluid chamber can comprise about 0.5 µL of the fluid. In certain embodiments, about 15 nL of the fluid can be exchanged between either the first haptic fluid chamber and the second haptic fluid chamber and the optic fluid chamber in response to pulses of the external energy directed at the composite material. In some embodiments, the fluid can be a silicone oil.

In another embodiment, an intraocular lens is disclosed comprising an optic portion and a peripheral portion coupled to the optic portion. The peripheral portion can comprise a first peripheral component and a second peripheral component. The first peripheral component can be made of a composite material comprising an energy absorbing constituent and a plurality of expandable components. The second peripheral component can also be made of the composite material comprising the energy absorbing constituent and the plurality of expandable components. A base power of the optic portion can be configured to increase in response to an external energy directed at the first peripheral component and the base power of the optic portion can be configured to decrease in response to the external energy directed at the second peripheral component. However, the base power of the optic portion can be configured to be unresponsive to forces applied to the peripheral portion by a capsular bag when the intraocular lens is implanted within the capsular bag.

In some embodiments, the optic portion can comprise an optic fluid chamber and the peripheral portion can comprise at least one peripheral fluid chamber in fluid communication with the optic fluid chamber. The base power can be configured to change in response to fluid displacement between the optic fluid chamber and the peripheral fluid chamber as a result of the external energy directed at the first peripheral component or the second peripheral component.

In some embodiments, the first peripheral component can be configured as a space-filler. The space-filler can be configured to expand in response to the external energy directed at the space-filler. Expansion of the space-filler can decrease a volume of the peripheral fluid chamber. For example, the space-filler can be configured as an expandable pad extending from either a chamber anterior wall or a chamber posterior wall.

In some embodiments, the second peripheral component can be configured as a chamber expander or jack. The chamber expander or jack can be configured to expand in response to the external energy directed at the chamber expander or jack. Expansion of the chamber expander or jack can increase a volume of the peripheral fluid chamber. For example, the chamber expander or jack can be configured as an expandable column extending from a chamber anterior wall to a chamber posterior wall.

In certain embodiments, the first peripheral component and the second peripheral component can be located within the same peripheral fluid chamber. In these embodiments, the second peripheral component can be positioned distal to the first peripheral component within the same peripheral fluid chamber. Also, in these embodiments, the first peripheral component can be positioned proximal to the second peripheral component within the same peripheral fluid chamber. The first peripheral component can be positioned closer to a fluid channel connecting the optic fluid chamber to the peripheral fluid chamber than the second peripheral component.

The first peripheral component and the second peripheral component can be configured as discrete peripheral components such that directing the external energy at one discrete peripheral component can cause a change in the base power of the optic portion and directing the external energy at another discrete peripheral component can also cause a change in the base power of the optic portion.

In some embodiments, one peripheral fluid chamber can comprise at least ten first peripheral components. In these and other embodiments, the same or another peripheral fluid chamber can comprise at least ten second peripheral components.

A method of post-operatively adjusting an intraocular lens is also disclosed. The method can comprise adjusting a base power of the intraocular lens by directing an external energy at a composite material within a peripheral portion of the intraocular lens. The peripheral portion can be coupled to an optic portion disposed radially inward of the peripheral portion. The composite material can comprise an energy absorbing constituent and a plurality of expandable components. The base power of the intraocular lens can be configured to be unresponsive to forces applied to the peripheral portion by a capsular bag when the intraocular lens is implanted within the capsular bag.

The optic portion can comprise an optic fluid chamber and the peripheral portion can comprise at least one peripheral fluid chamber in fluid communication with the optic fluid chamber. The base power of the intraocular lens can change in response to fluid displacement between the optic fluid chamber and the peripheral fluid chamber as a result of the external energy directed at the composite material. In some embodiments, about 15 nL of fluid can be exchanged between the peripheral fluid chamber and the optic fluid chamber in response to pulses of the external energy directed at the composite material.

In some embodiments, adjusting the base power of the intraocular lens can further comprise increasing the base power by directing the external energy at the composite material configured as a space-filler positioned within a peripheral fluid chamber defined within the peripheral portion.

The method can also comprise decreasing the base power by directing the external energy at another instance of the composite material configured as a chamber expander positioned within the peripheral portion.

In some embodiments, adjusting the base power of the intraocular lens can further comprise decreasing the base power by directing the external energy at the composite material configured as a chamber expander positioned within a peripheral fluid chamber defined within the peripheral portion. Decreasing the base power can further comprise directing the external energy at another instance of the composite material configured as a space-filler positioned within the peripheral fluid chamber.

In certain embodiments, adjusting the base power of the intraocular lens can further comprise directing pulses of the external energy at a first peripheral component within a peripheral fluid chamber defined within the peripheral portion and directing additional pulses of the external energy at a second peripheral component within the same peripheral fluid chamber. The first peripheral component can be made of the composite material and the second peripheral component can be made of the same composite material.

In additional embodiments, adjusting the base power of the intraocular lens can further comprise directing pulses of the external energy at a first peripheral component within a first peripheral fluid chamber defined within the peripheral portion and directing additional pulses of the external energy at a second peripheral component within a second peripheral fluid chamber defined within the peripheral portion. The first peripheral component can be made of the composite material and the second peripheral component can be made of the same composite material. The first peripheral fluid chamber can be in fluid communication with the second peripheral fluid chamber via an optic fluid chamber defined within the optic portion.

In some embodiments, adjusting the base power in a first direction can further comprise directing the external energy at a first composite material and adjusting the base power in a second direction by directing the external energy at a second composite material. The first composite material can comprise a first energy absorbing constituent having a first color. The second composite material can comprise a second energy absorbing constituent having a second color different from the first color.

DETAILED DESCRIPTION

Figure 1A:
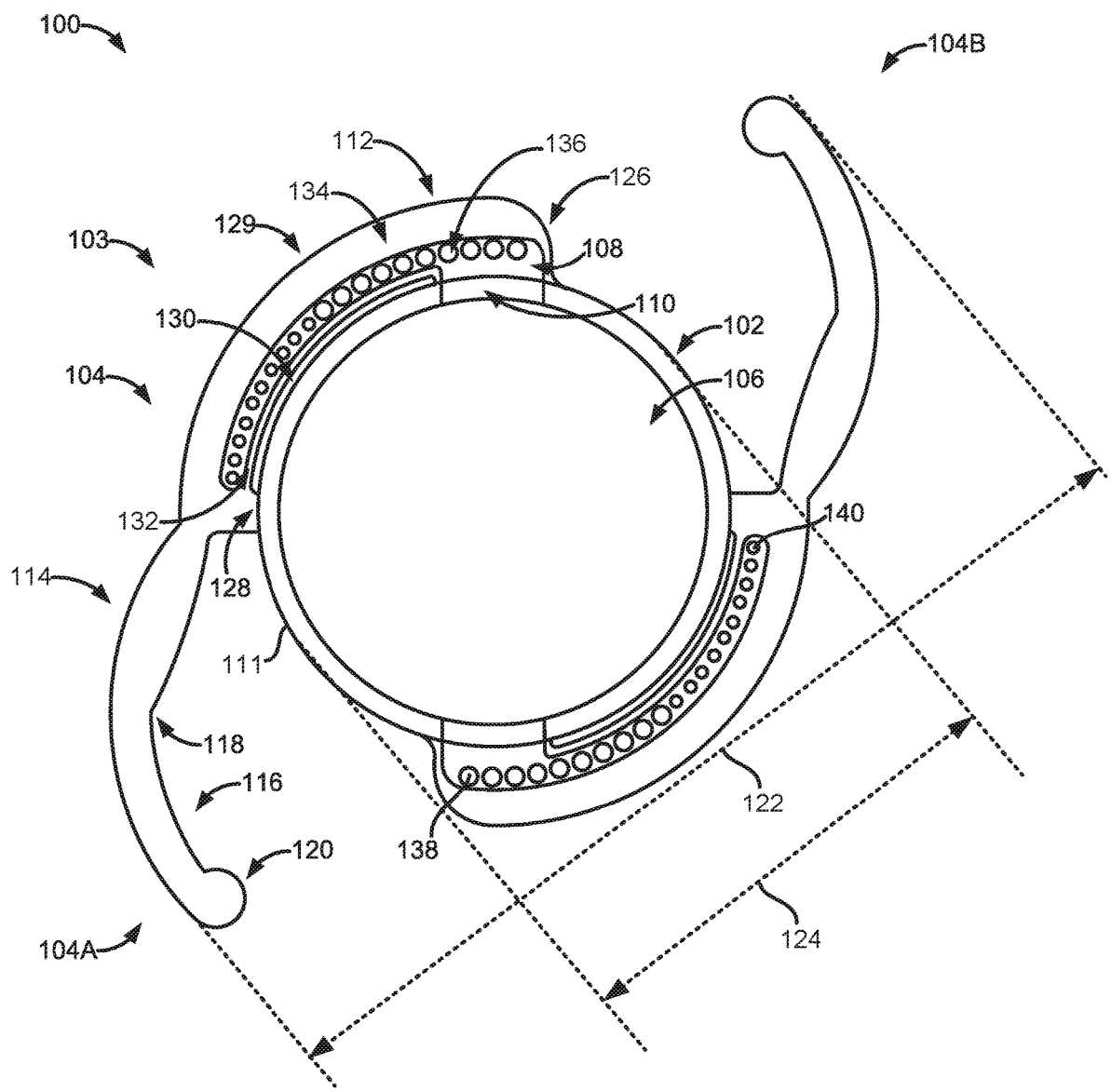
FIG. 1A illustrates a top plan view of an embodiment of an adjustable intraocular lens (IOL) with part of an anterior portion of the adjustable IOL removed to better illustrate components within the IOL.

FIG. 1A illustrates a top plan view of an embodiment of an adjustable static-focus intraocular lens (IOL) 100 with part of an anterior portion of the adjustable IOL 100 removed to better illustrate components within the IOL. As depicted in FIG. 1A, the adjustable IOL 100 can comprise an optic portion 102 and a peripheral portion 103. The peripheral portion 103 can comprise one or more haptics 104 including a first haptic 104A and a second haptic 104B extending peripherally from or coupled to the optic portion 102.

For example, the adjustable IOL 100 can be a one-piece lens (see, e.g., FIGS. 1A-3B) such that the peripheral portion 103 is connected to and extends from the optic portion 102. In this example embodiment, the peripheral portion 103 is formed along with the optic portion 102 and is not adhered or otherwise coupled to the optic portion 102 in a subsequent step.

In other embodiments, the peripheral portion 103 is coupled to and adhered to the optic portion 102. For example, the peripheral portion 103 can be adhered to the optic portion 102 after each is formed separately.

The optic portion 102 can comprise an optic fluid chamber 106 (see also, e.g., FIGS. 2B, 3A, and 3B) and one or more peripheral fluid chambers 108 in fluid communication with the optic fluid chamber 106. The one or more peripheral fluid chambers 108 can be defined within the peripheral portion 103. For example, the at least one peripheral fluid chamber 108 can extend into the peripheral portion 103.

In some embodiments, the at least one peripheral fluid chamber 108 can extend only partially into the peripheral portion 103. For example, the at least one peripheral fluid chamber 108 can extend only partially into one-third, one-half, or three-quarters of the peripheral portion 103. Also, for example, the at least one peripheral fluid chamber 108 can extend only partially into between one-third and one-half of the peripheral portion 103 or between one-half and three-quarters of the peripheral portion 103.

In certain embodiments, the at least one peripheral fluid chamber 108 can extend only partially into one of the haptics 104 of the peripheral portion 103. For example, the at least one peripheral fluid chamber 108 can extend only partially into one-third, one-half, or three-quarters of the haptic 104. Also, for example, the at least one peripheral fluid chamber 108 can extend only partially into between one-third and one-half of the haptic 104 or between one-half and three-quarters of the haptic 104.

As shown in FIG. 1A, the peripheral portion 103 can comprise two haptics 104 (e.g., a first haptic 104A and a second haptic 104B). In this embodiment, a peripheral fluid chamber 108 can extend into each of the two haptics 104. The peripheral fluid chamber 108 can extend only partially into haptic 104.

The one or more peripheral fluid chambers 108 can also be referred to as one or more haptic fluid chambers. When the peripheral portion 103 comprises a first haptic 104A and a second haptic 104B, the peripheral portion 103 can comprise one peripheral fluid chamber 108 referred to as a first haptic fluid chamber and another peripheral fluid chamber 108 referred to as a second haptic fluid chamber.

At least one of the haptics 104 (e.g., the first haptic 104A, the second haptic 104B, or a combination thereof) can be curved. In these embodiments, the peripheral fluid chamber 108 (e.g., the haptic fluid chamber) can be curved. The peripheral fluid chamber 108 can follow a curvature of the haptic 104. The peripheral fluid chamber 108 can also follow a curvature of the optic portion 102 when at least a segment of the haptic 104 follows a curvature of at least part of the optic portion 102.

The peripheral fluid chamber 108 can be in fluid communication with the optic fluid chamber 106 or fluidly coupled to the optic fluid chamber 106 via a fluid channel 110. The fluid channel 110 can be a passageway or conduit connecting the peripheral fluid chamber 108 to the optic fluid chamber 106. The fluid channel 110 can be defined along the posterior element 300 (see, e.g., FIGS. 3A and 3B) of the optic portion 102.

The fluid channel 110 can also refer to a gap or opening defined along a lateral side 111 or lateral surface (see also, e.g., FIGS. 2A, 2B, 3A, and 3B) of the optic portion 102. The fluid channel 110 can be curved. The fluid channel 110 can be substantially shaped as an annular segment.

The peripheral fluid chamber 108 can be in fluid communication with the optic fluid chamber 106 or fluidly coupled to the optic fluid chamber 106 via a singular fluid channel 110. When the adjustable IOL 100 comprises multiple peripheral fluid chambers 108, each of the peripheral fluid chambers 108 can be in fluid communication with the optic fluid chamber 106 or fluidly coupled to the optic fluid chamber 106 via a singular fluid channel 110.

In other embodiments, the peripheral fluid chamber 108 can be in fluid communication with the optic fluid chamber 106 or fluidly coupled to the optic fluid chamber 106 via a plurality (e.g., two or more) of fluid channels. In these embodiments, the two or more fluid channels 110 can be separated by a channel divider or dividing wall.

When the peripheral portion 103 comprises a first haptic 104A having a first haptic fluid chamber and a second haptic 104B having a second haptic fluid chamber, the first haptic fluid chamber can be in fluid communication or fluidly coupled to the optic fluid chamber 106 via a first fluid channel and the second haptic fluid chamber can be in fluid communication or fluidly coupled to the optic fluid chamber 106 via a second fluid channel. In these embodiments, the first fluid channel can be positioned diametrically opposed to the second fluid channel (see, e.g., FIGS. 1A, 1B, 2B, and 3A).

FIG. 1A illustrates that when the peripheral portion 103 is implemented as one or more haptics 104, each of the haptics 104 can have a haptic proximal portion 112 and a haptic distal portion 114. The peripheral fluid chamber 108 or the haptic fluid chamber can be defined within the haptic proximal portion 112.

At least a segment of the haptic proximal portion 112 can be curved. At least a segment of the haptic proximal portion 112 can follow a curvature of at least part of the optic portion 102.

The haptic distal portion 114 can comprise a haptic distal arm 116. The haptic distal arm 116 can be unattached to the optic portion 102 except via the haptic proximal portion 112.

The haptic distal arm 116 can comprise a kink or bend 118 defined along the haptic distal arm 116. The kink or bend 118 can allow the haptic distal arm 116 to compress or flex in response to capsular bag reshaping. The haptic distal arm 116 can terminate at a free or unconnected haptic distal end 120.

When the peripheral portion 103 comprises two haptics 104 (e.g., a first haptic 104A and a second haptic 104B), the adjustable IOL 100 can have an uncompressed haptic length 122 as measured from a haptic distal end 120 of the first haptic 104A to the haptic distal end 120 of the second haptic 104B. The uncompressed haptic length 122 can be between about 12.0 mm and about 14.0 mm. For example, the uncompressed haptic length 122 can be about 13.0 mm.

The haptic distal end 120 of each of the haptics 104 can be a closed end of the haptic 104 unconnected to the optic portion 102. The haptic distal end 120 can comprise a bulbous feature or nodule at the terminus of the haptic distal end 120.

As shown in FIG. 1A, the optic portion 102 can have an optic portion diameter 124. The optic portion diameter 124 can be between about 5.0 mm and 8.0 mm. For example, the optic portion diameter 124 can be about 6.0 mm.

The haptic 104 can be connected to the optic portion 102 at a proximal end 126 of the haptic 104. The haptic 104 can also be connected to the optic portion 102 at a distal connecting portion 128. The distal connecting portion 128 can be portion of the haptic 104 located distally of a distal end of the peripheral fluid chamber 108 or haptic fluid chamber.

A segment of the haptic 104 in between the proximal end 126 and the distal connecting portion 128 (herein referred to as a chamber segment 129) can be physically separated from the optic portion 102. The chamber segment 129 can comprise at least a segment of the peripheral fluid chamber 108 in between a radially inner chamber wall 132 and a radially outer chamber wall 134. For example, the radially inner chamber wall 132 of the chamber segment 129 can be separated from the optic portion 102 by an elongate gap or space. The elongate gap or space can be a curved gap 130, as shown in FIG. 1A.

The curved gap 130 can allow the peripheral fluid chamber 108 or haptic fluid chamber to expand or change shape without the radially inner chamber wall 132 impinging against or applying pressure to the lateral side 111 (see also, e.g., FIGS. 2A, 2B, 3A, and 3B) of the optic portion 102 adjacent to the chamber segment 129.

As shown in FIG. 1A, the radially outer chamber wall 134 can be thicker or bulkier than the radially inner chamber wall 132. In some embodiments, the radially outer chamber wall 134 can be thicker or bulkier than both the radially inner chamber wall 132 and the peripheral fluid chamber 108.

The thick or bulky radially outer chamber wall 134 can provide the chamber segment 129 with stiffness or resiliency when forces are applied to the chamber segment 129 in the radial direction by capsular bag contraction or reshaping. For example, the thick or bulky radially outer chamber wall 134 can allow the chamber segment 129 of the peripheral portion 103 to be insensitive or be less sensitive to radial forces applied to the peripheral portion 103 in the radial direction by capsular bag reshaping caused by ciliary muscle movements.

In some embodiments, the distal connecting portion 128 can be unfixed or unconnected to an adjacent section of the optic portion 102, thus allowing a greater amount of the haptic 104 to freely move for folding or splaying purposes during implantation of the IOL 100. Once the IOL 100 is implanted within the capsular bag, the distal connecting portion 128 can rest against or otherwise contact the adjacent section of the optic portion 102 to stabilize the haptic 104 and prevent the haptic 104 from twisting or otherwise moving around in response to capsular bag contractions or reshaping. In other embodiments, the haptic 104 can also be connected to the optic portion 102 at the distal connecting portion 128.

As shown in FIG. 1A, the peripheral fluid chamber 108 can terminate before reaching the haptic distal portion 114. In some embodiments, the haptic distal arm(s) 116 can be made of the same material as the haptic chamber walls.

One technical problem faced by the applicants is how to design a fluid-filled IOL that can be adjusted post-operatively by a clinician or other medical professional, but that would not be responsive to, or thus insensitive to, radial forces applied to the fluid-filled IOL by the capsular bag. One solution discovered by the applicants is the adjustable IOL disclosed herein with a peripheral fluid chamber that extends only partially into the haptic of the adjustable IOL and a chamber segment of the haptic having a radially outer chamber wall thicker than a radially inner chamber wall and the radially inner chamber wall separated from the optic portion by an elongate gap or space. The haptic can also be connected to the optic portion at a haptic proximal end and a distal connecting portion located distally of the chamber segment.

The peripheral portion 103 can comprise a composite material 400 (see, e.g., FIG. 4A) or at least part of the peripheral portion 103 can be made of the composite material 400. As will be discussed in more detail in the following sections, the composite material 400 can comprise an energy absorbing constituent 404 and a plurality of expandable components 406 (see, e.g., FIGS. 4A and 4B).

In some embodiments, the composite material 400 can be configured as a plurality of space-fillers 310 (see, e.g., FIGS. 3A and 3B) or pistons. One or more of the space-fillers 310 can be configured to expand in response to an external energy 318 (see, e.g., FIG. 3C) directed at the one or more space-fillers 310. Expansion of the one or more space-fillers 310 can decrease a volume of a peripheral fluid chamber 108 housing the one or more space-fillers 310. At least one of the space-fillers 310 can be configured as a pad extending from either a chamber anterior wall 314 or a chamber posterior wall 316 of the peripheral fluid chamber 108 (see, e.g., FIG. 3B).

In these and other embodiments, the composite material 400 can be configured as a plurality of chamber expanders 312 (see, e.g., FIG. 3B) or jacks. One or more of the chamber expanders 312 can be configured to expand in response to an external energy 318 (see, e.g., FIG. 3D) directed at the one or more chamber expanders 312. Expansion of the one or more chamber expanders 312 can increase a volume of the peripheral fluid chamber 108 housing the one or more chamber expanders 312. At least one of the chamber expanders 312 can be configured as an expandable column extending from a chamber anterior wall 314 to a chamber posterior wall 316 of the peripheral fluid chamber 108 (see, e.g., FIG. 3B).

A base power or optical/dioptric power of the optic portion 102 can be configured to change in response to an external energy 318 (see, e.g., FIGS. 3C and 3D) directed at the composite material 400. However, the base power of the optic portion 102 can be unresponsive or insensitive to forces applied to the peripheral portion 103 by the capsular bag when the adjustable IOL 100 is implanted within the capsular bag.

The base power of the optic portion 102 can be configured to change in response to fluid being displaced between the optic fluid chamber 106 and the peripheral fluid chamber 108 as a result of the external energy 318 directed at the composite material 400.

The composite material 400 of the peripheral portion 103 can be formed, shaped, or otherwise configured as a plurality of discrete peripheral components 136. For example, each of the peripheral components 136 can be separated from neighboring or adjacent peripheral components 136 by spaces or gaps.

The peripheral components 136 can be positioned or located within the peripheral fluid chamber(s) 108. In some embodiments, the peripheral components 136 can occupy the entire chamber length of the peripheral fluid chamber 108. In other embodiments, the peripheral components 136 can occupy only part of the peripheral fluid chamber 108.

In some embodiments, directing external energy 318 at one of the peripheral components 136 can cause that particular peripheral component 136 to change its shape or expand without substantially affecting the other peripheral components 136. For example, directing the external energy 318 at one of the peripheral components 136 can cause that particular peripheral component 136 to change its shape or expand without causing a similar shape change or expansion in the other peripheral components 136.

Pulses or a set amount of the external energy 318 can be directed at one peripheral component 136 in order to cause a change in the base power of the optic portion 102. In these embodiments, additional pulses or an additional amount of the external energy 318 can be directed at another peripheral component 136 in order to cause another change in the base power of the optic portion 102.

In some embodiments, the peripheral portion 103 can comprise between 20 and 40 peripheral components 136. In other embodiments, the peripheral portion 103 can comprise between 10 and 20 peripheral components 136. In additional embodiments, the peripheral portion 103 can comprise between 40 and 60 peripheral components 136.

In certain embodiments, one peripheral fluid chamber 108 can comprise 20 peripheral components 136. In other embodiments, one peripheral fluid chamber 108 can comprise between 10 and 20 peripheral components 136. In further embodiments, one peripheral fluid chamber 108 can comprise between 20 and 30 peripheral components 136. In additional embodiments, one peripheral fluid chamber 108 can comprise between 5 and 10 peripheral components 136.

The peripheral components 136 can comprise one or more first peripheral components 138, one or more second peripheral components 140, or a combination thereof. The first peripheral component(s) 138 and the second peripheral component(s) 140 can be positioned or located within the same peripheral fluid chamber 108.

In some embodiments, one peripheral fluid chamber 108 can comprise at least ten first peripheral components 138. In other embodiments, one peripheral fluid chamber 108 can comprise between five and ten first peripheral components 138 or between ten and twenty first peripheral components 138.

In these and other embodiments, one peripheral fluid chamber 108 can comprise at least ten second peripheral components 140. In other embodiments, one peripheral fluid chamber 108 can comprise between five and ten second peripheral components 140 or between ten and twenty second peripheral components 140.

In the embodiment shown in FIG. 1A, one peripheral fluid chamber 108 can comprise ten first peripheral components 138 and ten second peripheral components 140. Moreover, the adjustable IOL 100 can comprise two haptics 104 with each haptic comprising a haptic fluid chamber having ten first peripheral components 138 and ten second peripheral components 140.

The first peripheral components 138 can be positioned proximal to the second peripheral components 140 within the peripheral fluid chamber 108 (that is, the second peripheral components 140 can be positioned deeper within the peripheral fluid chamber 108). For example, the first peripheral components 138 can be positioned closer to a fluid channel 110 connecting the optic fluid chamber 106 to the peripheral fluid chamber 108 than the second peripheral components 140. One reason to position the second peripheral components 140 (e.g., the chamber expanders 312 or jacks) deeper or more distal in the peripheral fluid chamber 108 is to minimize the mechanical stresses placed on the optic portion 102 (which can cause unwanted aberrations) since expansion of the second peripheral components 140 affects the whole cross-section of the peripheral fluid chamber 108.

In other embodiments, at least some of the second peripheral components 140 can be positioned more proximal or closer to the fluid channel 110 than the first peripheral components 138. In further embodiments, the first peripheral components 138 can be interleaved with the second peripheral components 140 such that the components form an alternating pattern.

In the embodiment shown in FIG. 1A, the peripheral components 136 (including the first peripheral components 138, the second peripheral components 140, or a combination thereof) can be arranged in a single file (e.g., a single curved file) along a length of the peripheral fluid chamber 108. In other embodiments not shown in the figures but contemplated by this disclosure, the peripheral components 136 can be arranged in a zig-zag, a winding pattern, or a double or triple file pattern, i.e., two or more adjacent rows of peripheral components 136.

The base power of the optic portion 102 can be configured to change in response to fluid displacement between the optic fluid chamber 106 and the peripheral fluid chamber 108 as a result of an external energy 318 directed at the peripheral component(s) 136. For example, fluid can flow out of the peripheral fluid chamber 108 and into the optic fluid chamber 106 or flow out of the optic fluid chamber 106 and back into the peripheral fluid chamber 108 in response the external energy 318 directed at the peripheral component(s) 136.

The base power of the optic portion 102 can be configured to change in a first direction in response to an external energy 318 directed at the first peripheral component 138. The base power of the optic portion 102 can also be configured to change in a second direction opposite the first direction in response to an external energy 318 directed at the second peripheral component 140.

For example, the base power of the optic portion 102 can be configured to increase in response to external energy 318 directed at the first peripheral component 138. As a more specific example, fluid within the peripheral fluid chamber 108 can flow into the optic fluid chamber 106 in response to the external energy directed at the first peripheral component 138.

Also, for example, the base power of the optic portion 102 can be configured to decrease in response to external energy 318 directed at the second peripheral component 140. As a more specific example, fluid within the optic fluid chamber 106 can flow into the peripheral fluid chamber 108 in response to the external energy directed at the second peripheral component 140.

As will be discussed in more detail in the following sections, the first peripheral component 138 can be configured as a space-filler 310 (see, e.g., FIGS. 3A and 3B) or piston. The space-filler 310 can be configured to expand in response to external energy 318 directed at the space-filler 310. Expansion of the space-filler 310 can decrease a volume of the peripheral fluid chamber 108, which may therefore cause fluid to migrate from the peripheral fluid chamber 108 to the optic fluid chamber 106.

The second peripheral component 140 can be configured as a chamber expander 312 (see, e.g., FIGS. 2B, 3A, and 3B) or jack. The chamber expander 312 can be configured to expand in response to external energy 318 directed at the chamber expander 312. Expansion of the chamber expander 312 can increase a volume of the peripheral fluid chamber 108.

In some embodiments, the fluid within the optic fluid chamber 106, the peripheral fluid chamber(s) 108, or a combination thereof can be an oil. More specifically, in certain embodiments, the fluid within the optic fluid chamber 106, the peripheral fluid chamber(s) 108, or a combination thereof can be a silicone oil or fluid.

The fluid within the optic fluid chamber 106, the peripheral fluid chamber(s) 108, or a combination thereof can be a silicone oil or fluid comprising or made in part of diphenyl siloxane and dimethyl siloxane. In other embodiments, the silicone oil or fluid can comprise or be made in part of a ratio of two dimethyl siloxane units to one diphenyl siloxane unit. In certain embodiments, the silicone oil can comprise about 20 mol % diphenyl siloxane and about 80 mol % dimethyl siloxane.

More specifically, in some embodiments, the silicone oil can comprise diphenyltetramethyl cyclotrisiloxane. In additional embodiments, the silicone oil or fluid can comprise or be made in part of a diphenyl siloxane and dimethyl siloxane copolymer.

The fluid (e.g., the silicone oil) can be index matched with the lens body material used to make the optic portion 102. When the fluid is index matched with the lens body material, the entire optic portion 102 containing the fluid acts as a single lens. For example, the fluid can be selected so that it has a refractive index of between about 1.48 and 1.53 (or between about 1.50 and 1.53). In some embodiments, the fluid (e.g., the silicone oil) can have a polydispersity index of between about 1.2 and 1.3. In other embodiments, the fluid (e.g., the silicone oil) can have a polydispersity index of between about 1.3 and 1.5. In other embodiments, the fluid (e.g., the silicone oil) can have a polydispersity index of between about 1.1 and 1.2. Other example fluids are described in U.S. Patent Publication No. 2018/0153682, which is herein incorporated by reference in its entirety.

Figure 1B:
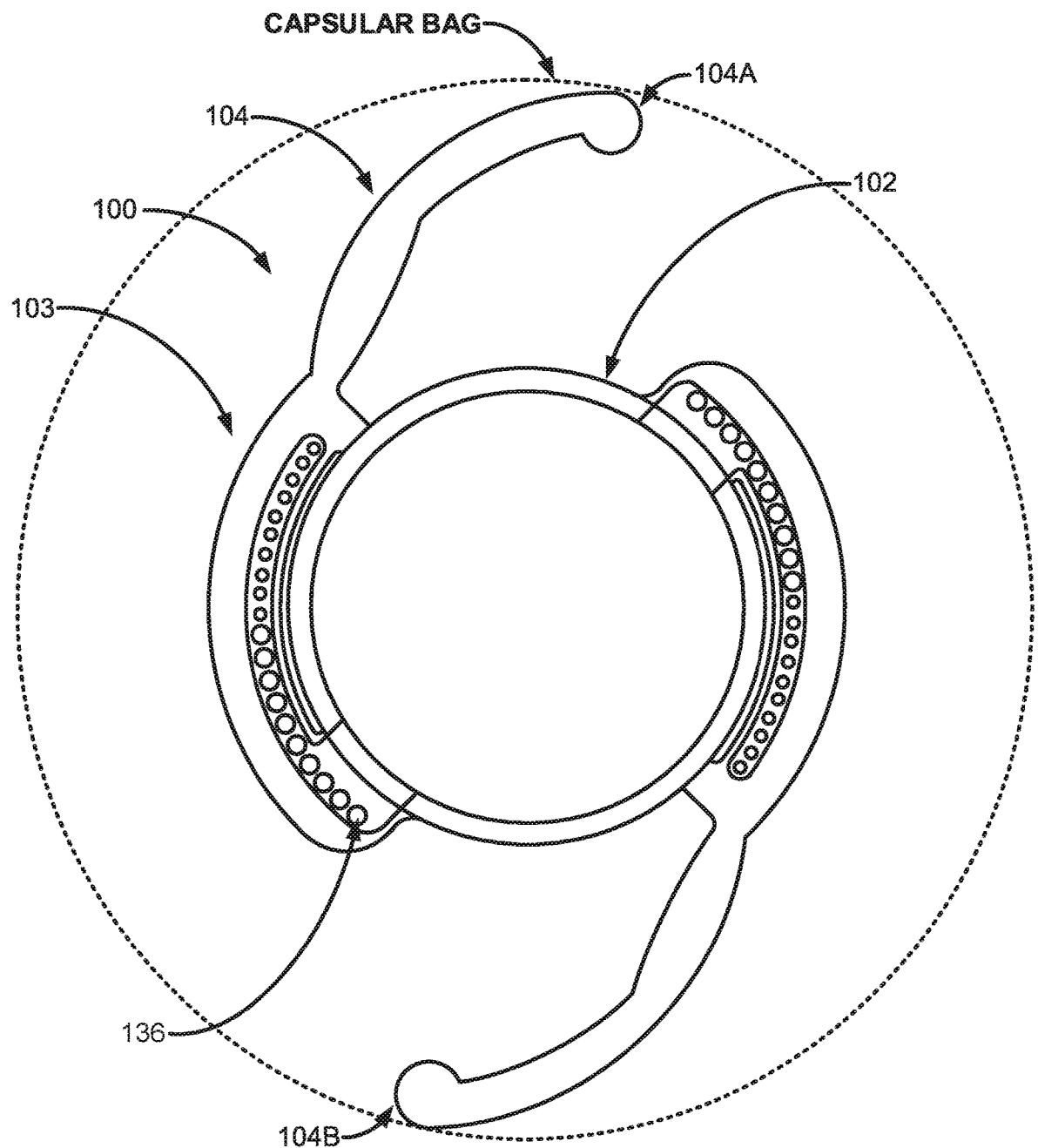
FIG. 1B illustrates the adjustable IOL implanted within a capsular bag of a subject.

FIG. 1B illustrates that the adjustable static-focus IOL 100 can be implanted within a native capsular bag in which a native lens has been removed. When implanted within the native capsular bag, the optic portion 102 can be adapted to refract light that enters the eye onto the retina. The one or more haptics 104 (e.g., the first haptic 104A and the second haptic 104B) can be configured to engage the capsular bag to hold the adjustable IOL 100 in place within the capsular bag.

Figure 2A:
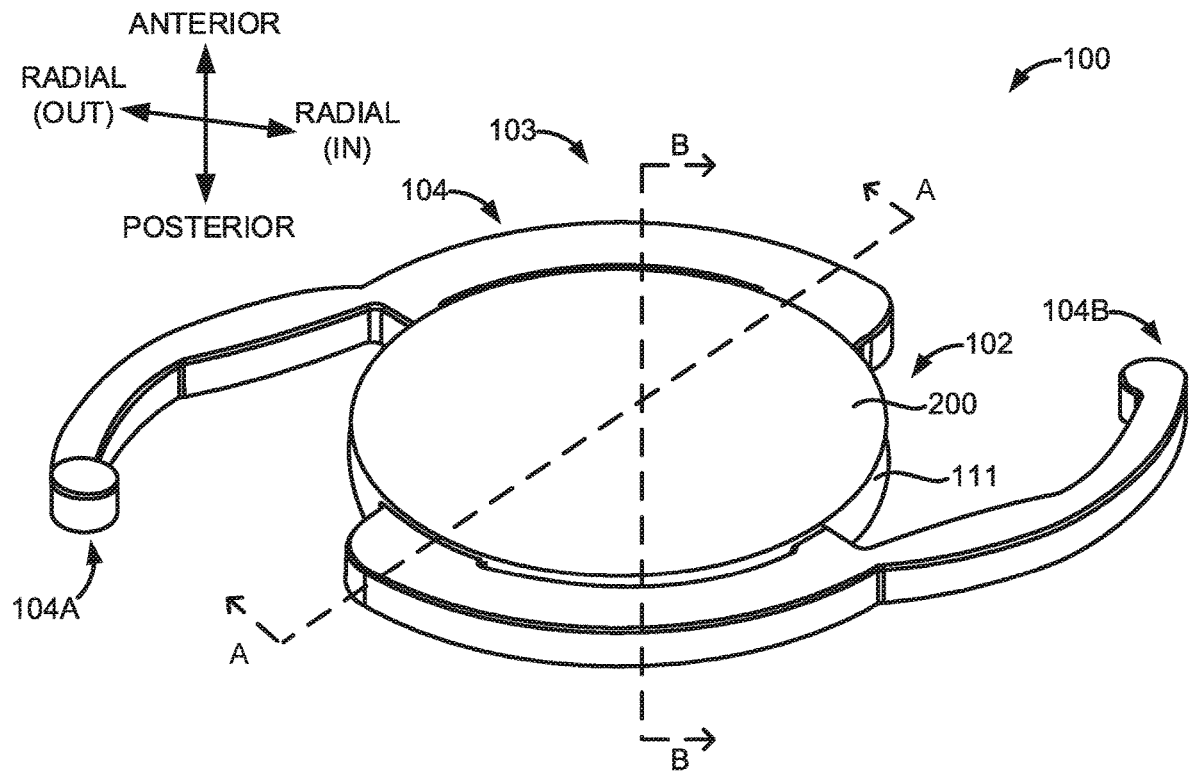
FIG. 2A illustrates a perspective view of the adjustable IOL.

FIG. 2A illustrates a perspective view of the adjustable IOL 100. As previously discussed, the optic fluid chamber 106 and the peripheral fluid chamber(s) 108 can be filled with a fluid (e.g., silicone oil). The base power of the optic portion 102 can be configured to change based on an internal fluid pressure within the fluid-filled optic fluid chamber 106.

The optic portion 102 can also be configured to change shape in response to fluid entering the optic fluid chamber 106. In certain embodiments, an anterior element 200 of the optic portion 102 can be configured to change shape in response to fluid entering or exiting the optic fluid chamber 106. For example, the anterior element 200 can be configured to increase its curvature in response to fluid entering the optic fluid chamber 106. Also, for example, the anterior element 200 can be configured to decrease its curvature in response to fluid exiting the optic fluid chamber 106.

In other embodiments, a posterior element 300 (see, e.g., FIGS. 3A and 3B) of the optic portion 102 can be configured to change shape (e.g., increase its curvature or decrease its curvature) in response to fluid entering or exiting the optic fluid chamber 106. In further embodiments, both the anterior element 200 and the posterior element 300 can be configured to change shape in response to the fluid entering or exiting the optic fluid chamber 106.

The base power of the optic portion 102 can be configured to increase or decrease in response to shape change(s) undertaken by the anterior element 200, the posterior element 300, or a combination thereof. Increasing the curvature of the anterior element 200, the posterior element 300, or a combination thereof can increase a base dioptric power of the optic portion 102 allowing for better near vision. Decreasing the curvature of the anterior element 200, the posterior element 300, or a combination thereof can decrease a base dioptric power of the optic portion 102 allowing for better distance vision.

For example, the base power of the optic portion 102 can be configured to increase as fluid enters the optic fluid chamber 106 from the peripheral fluid chamber(s) 108 (e.g., the haptic fluid chamber(s)). Fluid can flow from the peripheral fluid chamber(s) 108 into the optic fluid chamber 106 as the volume of the peripheral fluid chamber(s) 108 decreases in response to an expansion of one or more of the first peripheral components 138. One or more of the first peripheral components 138 can expand in response to an external energy 318 directed at the first peripheral component(s) 138.

Also, for example, the base power of the optic portion 102 can be configured to decrease as fluid exits or is drawn out of the fluid-filled optic fluid chamber 106 into the peripheral fluid chamber(s) 108. Fluid can flow from the optic fluid chamber 106 into the peripheral fluid chamber(s) 108 as the volume of the peripheral fluid chamber(s) 108 increases in response to an expansion of one or more of the second peripheral components 140. One or more of the second peripheral components 140 can expand in response to an external energy 318 directed at the second peripheral component(s) 140.

Figure 2B:
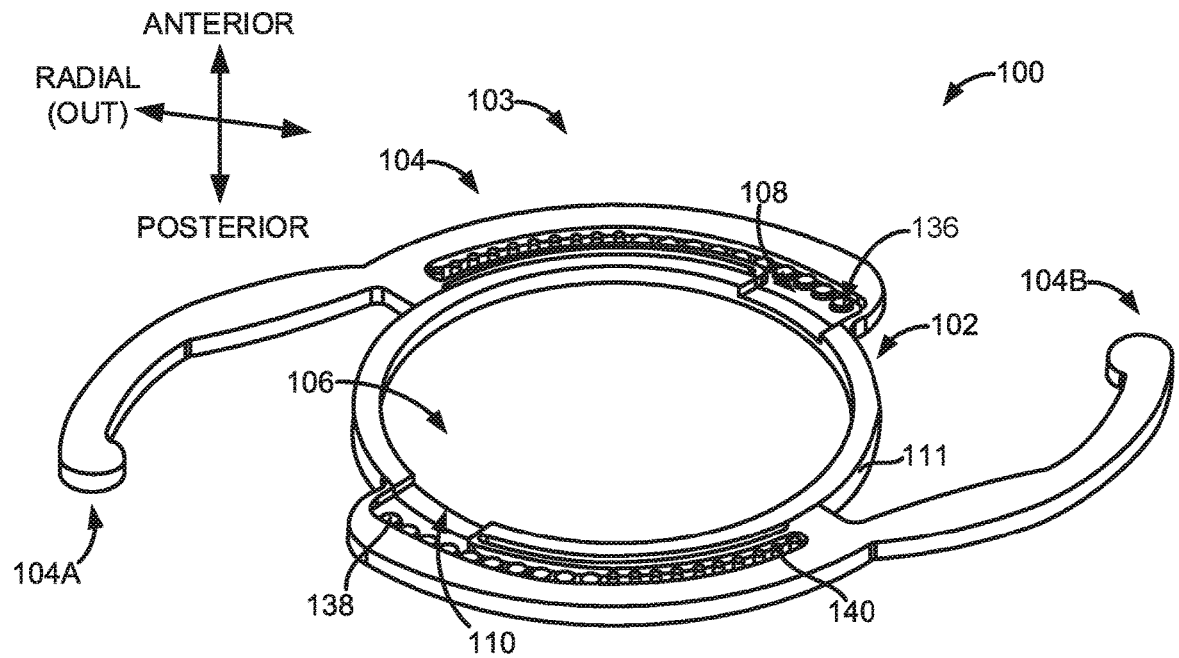
FIG. 2B illustrates a perspective view of the adjustable IOL with part of the anterior portion of the adjustable IOL removed to better illustrate components within the IOL.

FIG. 2B illustrates a perspective view of the adjustable IOL 100 with part of the anterior portion of the adjustable IOL 100 removed to better illustrate components within the IOL. The adjustable IOL 100 can comprise a peripheral portion 103 comprising a plurality of peripheral components 136 within the peripheral fluid chamber(s) 108. For example, parts of the peripheral portion 103 can be formed as the peripheral components 136.

As shown in FIG. 2B, the optic fluid chamber 106 can be in fluid communication with each of the peripheral fluid chambers 108 through a fluid channel 110. The fluid channel 110 can be a conduit or passageway connecting the optic fluid chamber 106 to the peripheral fluid chamber(s) 108 or haptic fluid chamber(s). Although a singular fluid channel 110 is shown connecting the optic fluid chamber 106 to each peripheral fluid chamber 108, it is contemplated by this disclosure that a plurality of fluid channels (e.g., two fluid channels) can connect the optic fluid chamber 106 to each peripheral fluid chamber 108.

The base power of the optic portion 102 can be configured to change (e.g., increase or decrease) in response to an external energy 318 directed at the peripheral components 136. As previously discussed, each of the peripheral components 136 can be made of the composite material 400.

As will be discussed in more detail in the following sections, each of the first peripheral components 138 can be configured as a space-filler 310 (see also, e.g., 3A, 3B, and 3C). The space-filler 310 can be configured to expand in response to external energy directed at the space-filler 310. Expansion of the space-filler 310 can decrease a volume of the peripheral fluid chamber 108 and causing the fluid to flow from the peripheral fluid chamber 108 into the optic fluid chamber 106.

Figure 3A:
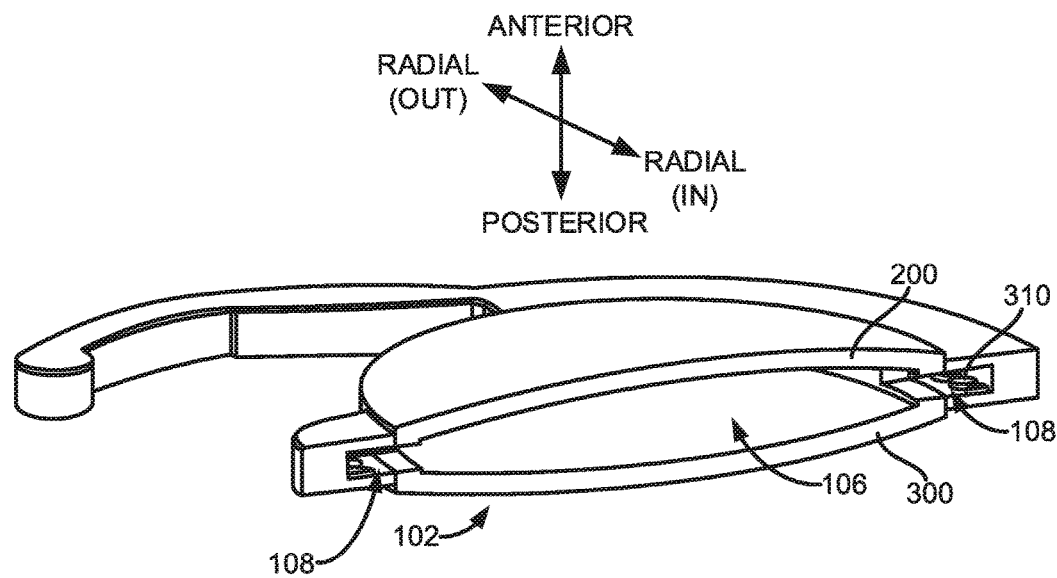
FIG. 3A illustrates a sectional view of the adjustable IOL taken along cross-section A-A of FIG. 2A.
Figure 3B:
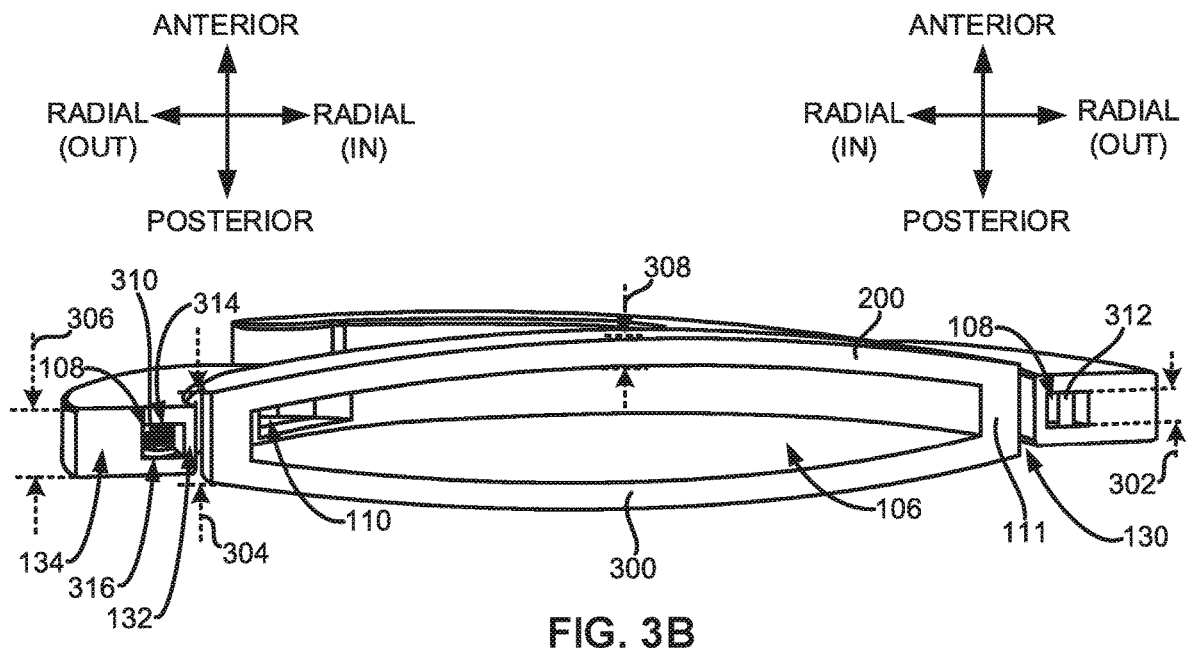
FIG. 3B illustrates a sectional view of the adjustable IOL taken along cross-section B-B of FIG. 2A.
Figure 3C:
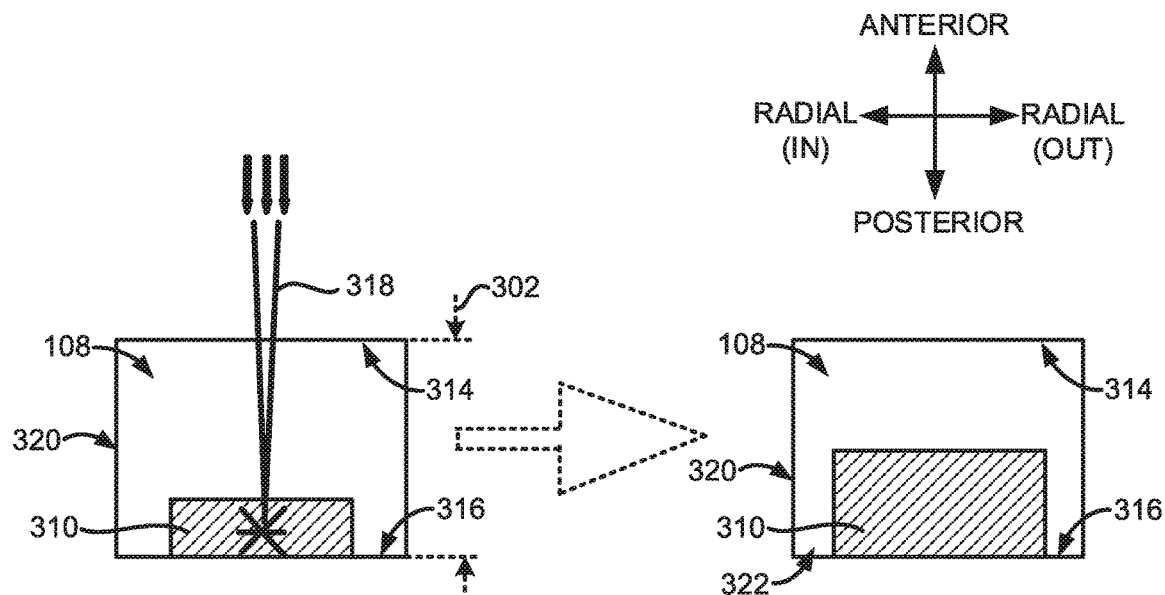
FIG. 3C illustrates an external energy directed at a first peripheral component of the adjustable IOL.
Figure 3D:
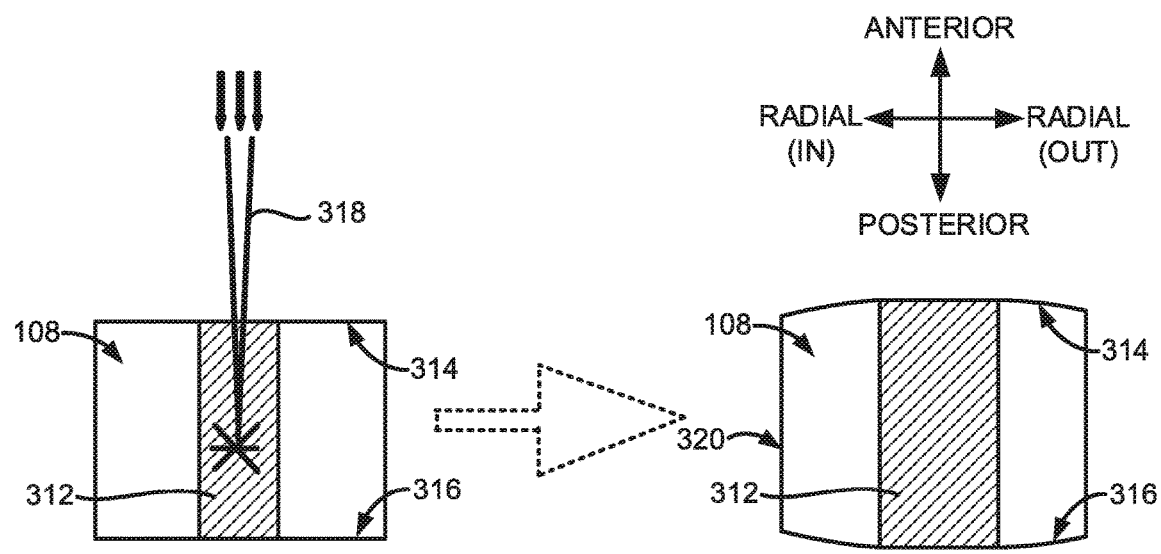
FIG. 3D illustrates an external energy directed at a second peripheral component of the adjustable IOL.

Each of the second peripheral components 140 can be configured as a chamber expander 312 (see also, e.g., FIGS. 3B and 3D). The chamber expander 312 can be configured to expand in response to external energy directed at the chamber expander 312. Expansion of the chamber expander 312 can increase a volume of the peripheral fluid chamber 108 by expanding the peripheral fluid chamber 108 and causing the fluid to flow or be drawn out from the optic fluid chamber 106 into the peripheral fluid chamber 108.

The optic fluid chamber 106 and the peripheral fluid chamber(s) 108 can comprise or hold a fluid (e.g., silicone oil) having a total fluid volume of between about 10 µL and about 20 µL. For example, the optic fluid chamber 106 and the peripheral fluid chamber(s) 108 can comprise a fluid (e.g., silicone oil) having a total fluid volume of about 15 µL.

In the embodiment shown in FIG. 2B, the peripheral portion 103 can comprise a first haptic 104A and a second haptic 104B. The first haptic 104A can have a first haptic fluid chamber and the second haptic 104B can have a second haptic fluid chamber. Each of the first haptic fluid chamber and the second haptic fluid chamber can be considered one of the peripheral fluid chambers 108. In this embodiment, each of the haptic fluid chambers (e.g., each of the first haptic fluid chamber and the second haptic fluid chamber) can comprise or hold a fluid having fluid volume of between about 0.3 µL and 0.6 µL (or about 0.5 µL).

In some embodiments, between about 10 nanoliters (nL) and 20 nL of the fluid can be exchanged or displaced between a peripheral fluid chamber 108 (for example, either the first haptic fluid chamber or the second haptic fluid chamber) and the optic fluid chamber 106 in response to pulses of the external energy 318 directed at one of the peripheral components 136. More specifically, about 15 nL of the fluid can be exchanged or displaced between one or more peripheral fluid chambers 108 (for example, either the first haptic fluid chamber or the second haptic fluid chamber) and the optic fluid chamber 106 in response to pulses of the external energy 318 directed at one of the peripheral components 136.

In some embodiments, the base power of the optic portion 102 can be configured to change between about 0.05 diopter (D) to about 0.5 D in either a positive or negative direction in response to pulses of the external energy 318 directed at one of the peripheral components 136. For example, the base power of the optic portion 102 can be configured to change by about 0.1 D in response to pulses of the external energy 318 directed at one of the peripheral components 136.

The change in the base power of the optic portion 102 can be a persistent or a substantially permanent change. A persistent or substantially permanent change can mean that the peripheral component 136 does not substantially revert back to its original shape or size after the change has occurred.

In certain embodiments, the base power of the optic portion 102 can be configured to change in total between about 1.0 D and about 2.0 D in either a positive or negative direction. In these embodiments, the total power change can be dictated by the total number of peripheral components 136, the size and/or expandable characteristics of the peripheral components 136, the chamber volume of the peripheral fluid chamber 108 and/or the optic fluid chamber 106, the volume of the oil within such chambers, or a combination thereof.

In other embodiments, the base power of the optic portion 102 can be configured to change in total between about 2.0 D and about 3.0 D in either a positive or negative direction. In additional embodiments, the base power of the optic portion 102 can be configured to change in total between about 3.0 D and about 5.0 D in either a positive or negative direction. In further embodiments, the base power of the optic portion 102 can be configured to change in total between about 5.0 D and about 10.0 D in either a positive or negative direction.

In some embodiments, the optic portion 102 can have an unfilled or as-manufactured optical power (i.e., an optical power of the optic portion 102 when the optic fluid chamber 106 is empty or unfilled) of between about 11 D and 13 D (a "zero power" lens). For example, the optic portion 102 can have an unfilled or as-manufactured optical power of about 12 D. The optical power of the optic portion 102 can increase as the optic fluid chamber 106 is filled with the fluid (e.g., the silicone oil).

The optic fluid chamber 106 can be filled until the base power of the filled optic portion 102 (as contributed by both the fluid and the lens surfaces of the optic portion 102) is between about 15 D (a low-powered IOL) to about 30 D (a high-powered IOL). For example, the optic fluid chamber 106 can be filled until the base power of the filled optic portion 102 is about 20 D.

The adjustable IOL 100 implanted within a capsular bag of the subject can have a base power between about 15 D to about 30 D (e.g., about 20 D). A clinician or medical professional can direct the external energy 318 (e.g., a laser light) at the peripheral components 136 to increase or decrease the base power of the optic portion 102 when the adjustable IOL 100 is implanted within the capsular bag of the subject.

For example, the adjustable IOL 100 can have a base power of about 20 D when implanted within the eye of the subject. If power correction is desired to increase the power of the lens, a clinician or medical professional can direct the external energy 318 at each of the first peripheral components 138 to increase the base power of the optic portion 102 stepwise between about +0.1 D and +0.2 D until the final base power is between about 21 D (+1.0 D change in total) and 22 D (+2.0 D change in total).

In other embodiments, the clinician or medical professional can direct the external energy 318 at each of the first peripheral components 138 to increase the base power of the optic portion 102 stepwise between about +0.1 D and +0.2 D until the final base power is between about 22 D (+2.0 D change in total) and 25 D (+5.0 D change in total).

As another example, the adjustable IOL 100 can have a base power of about 25 D when implanted within the eye of the subject. If power correction is desired to decrease the power of the lens, a clinician or medical professional can direct the external energy 318 at each of the second peripheral components 140 to decrease the base power of the optic portion 102 stepwise between about −0.1 D and −0.2 D until the final base power is between about 24 D (−1.0 D change in total) and 23 D (−2.0 D change in total).

In other embodiments, the clinician or medical professional can direct the external energy 318 at each of the second peripheral components 140 to decrease the base power of the optic portion 102 stepwise between about −0.1 D and −0.2 D until the final base power is between about 23 D (−2.0 D change in total) and 20 D (−5.0 D change in total).

In some embodiments, the adjustable IOL 100 can have an optic sensitivity of between about 100 nL to 200 nL (e.g., about 150 nL) of fluid displacement per diopter. That is, the base power of the optic portion 102 can change by about 1.0 D when between about 100 nL to 200 nL (e.g., about 150 nL) of the fluid is displaced between the peripheral fluid chamber 108 and the optic fluid chamber 106. As a more specific example, the base power of the optic portion 102 can increase by +1 D when between about 100 nL to 200 nL (e.g., about 150 nL) of the fluid enters the optic fluid chamber 106 from the peripheral fluid chamber 108 as a result of the external energy 318 directed at the first peripheral components 138. Moreover, the base power of the optic portion 102 can decrease by −1.0 D when between about 100 nL to 200 nL (e.g., about 150 nL) of the fluid exits or is drawn out of the optic fluid chamber 106 into the peripheral fluid chamber 108 as a result of the external energy 318 directed at the second peripheral components 140.

In certain embodiments, each of the peripheral fluid chambers 108 can comprise ten first peripheral components 138 and ten second peripheral components 140. In these embodiments, directing the external energy 318 at each of the first peripheral components 138 or each of the second peripheral components 140 can cause between about 10 nL and 20 nL (e.g., about 15 nL) of the fluid to be displaced or exchanged between the optic fluid chamber 106 and the peripheral fluid chamber 108. For example, directing the external energy 318 at one of the first peripheral components 138 can cause the first peripheral component 138 to expand and decrease the volume of the peripheral fluid chamber 108 housing the first peripheral component 138. This can cause between about 10 nL and about 20 nL (e.g., about 15 nL) of the fluid to flow from the peripheral fluid chamber 108 into the optic fluid chamber 106. Also, for example, directing the external energy 318 at one of the second peripheral components 140 can cause the second peripheral component 140 to expand and increase the volume of the peripheral fluid chamber 108 housing the second peripheral component 140. This can cause between about 10 nL and about 20 nL (e.g., about 15 nL) of the fluid to be drawn out of the optic fluid chamber 106 into the peripheral fluid chamber 108.

The adjustable IOL 100 can be configured such that the base power of the optic portion 102 changes between about 0.05 D and 0.5 D as a result of this fluid exchange or displacement. As a more specific example, the base power of the optic portion 102 can change by about 0.1 D in response to about 15 nL of the fluid being displaced or exchanged between the optic fluid chamber 106 and the peripheral fluid chamber 108.

FIG. 3A illustrates a sectional view of the adjustable IOL 100 taken along cross-section A-A of FIG. 2A. The optic portion 102 can comprise an anterior element 200 and a posterior element 300. A fluid-filled optic fluid chamber 106 can be defined in between the anterior element 200 and the posterior element 300.

The anterior element 200 can comprise an anterior optical surface and an anterior inner surface opposite the anterior optical surface. The posterior element 300 can comprise a posterior optical surface and a posterior inner surface opposite the posterior optical surface. Any of the anterior optical surface, the posterior optical surface, or a combination thereof can be considered and referred to as an external optical surface. The anterior inner surface and the posterior inner surface can face the optic fluid chamber 106. At least part of the anterior inner surface and at least part of the posterior inner surface can serve as chamber walls of the optic fluid chamber 106. In some embodiments, the peripheral portion 103 (e.g., the haptics 104) can be connected to or can extend from at least part of the posterior element 300 of the optic portion 102.

As will be discussed in more detail in the following sections, the adjustable IOL 100 can have a lens surface profile or pattern (e.g., a light-splitting lens profile or pattern) defined on the external optical surface. For example, the lens surface profile can comprise a diffractive surface profile or pattern or a phase-shifting structure or profile. The lens surface profile or pattern can allow the adjustable IOL 100 to be adapted for different use cases such as providing focus for one particular distance (monofocal) or focus for multiple distances (multifocal). For example, depending on the lens surface profile or pattern defined on the external optical surface, the adjustable IOL 100 can be configured as an adjustable monofocal IOL, an adjustable multifocal IOL (e.g., an adjustable bifocal or trifocal IOL), or an adjustable extended depth of focus (EDOF) IOL.

The optic portion 102 can be configured to deform, flex, or otherwise change shape in response to fluid entering or exiting the optic fluid chamber 106. In some embodiments, the anterior element 200 can be configured to deform, flex, or otherwise change shape (e.g., change its curvature) in response to fluid entering or exiting the optic fluid chamber 106. In other embodiments, the posterior element 300 can be configured to deform, flex, or otherwise change shape (e.g., change its curvature) in response to fluid entering or exiting the optic fluid chamber 106. In further embodiments, both the anterior element 200 and the posterior element 300 can be configured to deform, flex, or otherwise change their shape(s) in response to fluid entering or exiting the optic fluid chamber 106. The base power of the optic portion 102 can be configured to change in response to the shape change undertaken by the shape-changing components of the optic portion 102 (e.g., the anterior element 200, the posterior element 300, or a combination thereof).

The optic portion 102 can be made in part of a deformable or flexible material. In some embodiments, the optic portion 102 can be made in part of a deformable or flexible polymeric material. For example, the anterior element 200, the posterior element 300 or a combination thereof can be made in part of a deformable or flexible polymeric material. At least part of the peripheral portion 103, such as the one or more haptics 104 (e.g., the first haptic 104A, the second haptic 104B, or a combination thereof) can be made of the same deformable or flexible material as the optic portion 102. In other embodiments, the one or more haptics 104 can be made in part of different materials from the optic portion 102.

In some embodiments, the optic portion 102 and the parts of the peripheral portion 103 not made of the composite material 400 can comprise or be made in part of a polymer or a cross-linked copolymer comprising a copolymer blend.

For example, in some embodiments, the copolymer blend can comprise an alkyl acrylate or methacrylate, a fluoro-alkyl (meth)acrylate, a phenyl-alkyl acrylate, or a combination thereof. It is contemplated by this disclosure and it should be understood by one of ordinary skill in the art that these types of acrylic cross-linked copolymers can be generally copolymers of a plurality of acrylates or methacrylates. The term "acrylate" as used herein can be understood to mean acrylates or methacrylates unless otherwise specified.

For example, the optic portion 102 and the parts of the peripheral portion 103 not made of the composite material 400 can be made of hydrophobic acrylic materials. For example, the hydrophobic acrylic materials may comprise a hydrophobic acrylate/methacrylate copolymer. In some embodiments, the hydrophobic acrylic materials can comprise a combination of phenylethyl acrylate (PEA) and phenylethyl methacrylate (PEMA).

In one example embodiment, the cross-linked copolymer can comprise an alkyl acrylate in the amount of about 3% to 20% (wt %), a fluoro-alkyl acrylate in the amount of about 10% to 35% (wt %), and a phenyl-alkyl acrylate in the amount of about 50% to 80% (wt %). In some embodiments, the cross-linked copolymer can comprise or be made in part of an n-butyl acrylate as the alkyl acrylate, trifluoroethyl methacrylate as the fluoro-alkyl acrylate, and phenylethyl acrylate as the phenyl-alkyl acrylate. More specifically, the cross-linked copolymer can comprise n-butyl acrylate in the amount of about 3% to 20% (wt %) (e.g., between about 12% to 16%), trifluoroethyl methacrylate in the amount of about 10% to 35% (wt %) (e.g., between about 17% to 21%), and phenylethyl acrylate in the amount of about 50% to 80% (wt %) (e.g., between about 64% to 67%).

The final composition of the cross-linked copolymer can also comprise a cross-linker or cross-linking agent such as ethylene glycol dimethacrylate (EGDMA). For example, the final composition of the cross-linked copolymer can also comprise a cross-linker or cross-linking agent (e.g., EGDMA). The final composition of the cross-linked copolymer can also comprise an initiator or initiating agent (e.g., Perkadox 16, camphorquinone, 1-phenyl-1,2-propanedione, and 2-ethylhexyl-4-(dimenthylamino)benzoate)) and a UV absorber.

In some embodiments, the refractive index of the material used to make the optic portion 102 can be between about 1.48 and about 1.53. In certain embodiments, the refractive index of the material used to make the optic portion 102 can be between about 1.50 and about 1.53.

In some embodiments, the optic portion 102 and the parts of the peripheral portion 103 not made of the composite material 400 can comprise a a reactive (polymerizable) UV absorber and a reactive blue-light absorber. For example, the reactive UV absorber can be or comprise 2-(2'-hydroxy-3'-methallyl-5'-methylphenyl)benzotriazole, commercially available as o-Methallyl Tinuvin P ("oMTP") from Polysciences, Inc., Warrington, Pennsylvania, 3-(2H-benzo[d][1,2,3]triazol-2-yl)-4-hydroxyphenylethyl methacrylate, and 2-(3-(tert-butyl)-4-hydroxy-5-(5-methoxy-2H-benzo[d][1,2,3]triazol-2-yl)phenoxy)ethyl methacrylate. In certain embodiments, the reactive UV absorbers are present in an amount from about 0.1%-5% (wt %). When present, the reactive UV absorbers are typically present in an amount from about 1.5%-2.5% (wt %) or in an amount from about 1.5%-2% (wt %).

In certain embodiments, the reactive blue-light absorbing compounds can be those described in U.S. Pat. Nos. 5,470,932; 8,207,244; and 8,329,775, the entire contents of which are hereby incorporated by reference. For example, the blue-light absorbing dye can be N-2-[3-(2'-methylphenylazo)-4-hydroxyphenyl]ethyl methacrylamide. When present, blue-light absorbers are typically present in an amount from about 0.005%-1% (wt %) or in an amount from about 0.01%-0.1% (wt %).

FIG. 3B illustrates a sectional view of the adjustable IOL taken along cross-section B-B of FIG. 2A. As shown in FIG. 3B, the peripheral fluid chamber 108 can have a chamber height 302. In some embodiments, the chamber height 302 can be about 0.1 mm. In other embodiments, the chamber height 302 can be between about 0.1 mm and 0.3 mm.

In other embodiments, the chamber height 302 can be between about 0.3 mm and 1.0 mm. In further embodiments, the chamber height 302 can be between about 1.0 mm and 1.5 mm.

FIG. 3B also illustrates that the lateral side 111 of the optic portion 102 can have a side height 304 (as measured in the anterior-to-posterior direction). In some embodiments, the side height 304 can be between about 0.50 mm and 0.75 mm. For example, the side height 304 can be about 0.65 mm. In other embodiments, the side height 304 can be between about 0.40 mm and 0.50 mm or between about 0.75 mm and 1.25 mm.

The peripheral portion 103 can also have a peripheral portion height 306 (also referred to as haptic height or thickness). In some embodiments, the peripheral portion height 306 can be between about 0.50 mm and 0.60 mm. In other embodiments, the peripheral portion height 306 can be between about 0.60 mm and 0.65 mm or between about 0.45 mm and 0.50 mm.

As shown in FIG. 3B, the side height 304 of the lateral side 111 of the optic portion 102 can be greater than the peripheral portion height 306. For example, when the peripheral portion 103 comprises one or more haptics, the thickness or height of the haptics (as measured in an anterior-to-posterior direction) can be less than the thickness or height of the optic portion 102 along all sections of the optic portion 102.

In some embodiments, the peripheral portion height 306 or thickness (in an anterior-to-posterior direction) can be substantially uniform such that no part of the peripheral portion 103 is taller or thicker than any other part of the peripheral portion 103. When the peripheral portion 103 comprises multiple haptics 104, all of the haptics 104 can have the same height or thickness.

FIG. 3B also illustrates that the anterior element 200 can have an anterior element thickness 308 (as measured in the anterior-to-posterior direction). In some embodiments, the anterior element thickness 308 can be between about 0.15 mm and about 0.25 mm. For example, the anterior element thickness 308 can be about 0.20 mm.

FIGS. 3A and 3B also illustrate that the first peripheral component 138 can be configured as a space-filler 310. The space-filler 310 can be configured to expand in response to the external energy 318 directed at the space-filler 310. Expansion of the space-filler 310 can decrease a volume of the peripheral fluid chamber 108.

As a more specific example, the space-filler 310 can be implemented as an expandable pad extending from at least one of a chamber anterior wall 314 and a chamber posterior wall 316. The base power of the optic portion 102 can be configured to increase in response to the external energy 318 directed at the space-filler 310, resulting in fluid being displaced out of the peripheral fluid chamber 108 due to the increased volume of the space filler 310.

FIG. 3B also illustrates that the second peripheral component 140 can be configured as a chamber expander 312. The chamber expander 312 can be configured to expand in response to the external energy 318 directed at the chamber expander 312. Expansion of the chamber expander 312 can increase a volume of the peripheral fluid chamber 108.

As a more specific example, the chamber expander 312 can be implemented as an expandable column extending from the chamber anterior wall 314 to the chamber posterior wall 316. Expansion of the expandable column can increase the volume of the peripheral fluid chamber 108. The base power of the optic portion 102 can be configured to decrease in response to the external energy 318 directed at the expandable column, resulting in an expansion of the chamber expander 312 and an increase in the volume of the peripheral fluid chamber 108.

FIG. 3C illustrates that an external energy 318 can be directed at a space-filler 310 of the adjustable IOL 100 to induce a shape change in the space-filler 310.

The first peripheral component 138 can be made of the composite material 400. The first peripheral component 138 can be positioned within the peripheral fluid chamber 108.

In some embodiments, the composite material 400 used to make the first peripheral component 138 can be cured within the peripheral fluid chamber 108 along with the rest of the material used to construct the peripheral fluid chamber 108. In these embodiments, the first peripheral component 138 can be cured in place within the peripheral fluid chamber 108.

In other embodiments, the first peripheral component 138 can be adhered to an interior wall or surface of the peripheral fluid chamber 108 using an adhesive. The adhesive can be cured to secure the first peripheral component 138 to the interior wall or surface of the peripheral fluid chamber 108.

The first peripheral component 138 can be configured as a space-filler 310. In some embodiments, the space-filler 310 can be implemented as an expandable disk-shaped pad (see, e.g., FIGS. 2B, 3A, and 3B). Although the figures illustrate the space-fillers 310 shaped as substantially flat cylinders or disks, it is contemplated by this disclosure that the space-fillers 310 can be substantially shaped as spheres, hemispheres, ovoids, ellipsoids, cuboids or other polyhedrons, or a combination thereof.

The space-fillers 310 can extend from, be adhered to, or otherwise be coupled to either a chamber anterior wall 314 or a chamber posterior wall 316. In some embodiments, when the peripheral fluid chamber 108 comprises multiple space-fillers 310, at least one of the space-fillers 310 can extend from, be adhered to, or otherwise be coupled to the chamber anterior wall 314 and another of the space-fillers 310 can extend from, be adhered to, or otherwise be coupled to the chamber posterior wall 316.

In other embodiments, the space-fillers 310 can extend from, be adhered to, or otherwise be coupled to a chamber interior lateral wall 320.

As shown in FIG. 3C, the space-filler 310 can expand in response to a burst of the external energy 318 directed at the space-filler 310. Expansion of the space-filler 310 can decrease an internal volume of the peripheral fluid chamber 108 and displace fluid from the peripheral fluid chamber 108 into the optic fluid chamber 106. The base power of the optic portion 102 can be configured to increase in response to the external energy 318 directed at the space-filler 310.

FIG. 3C illustrates that the space-filler 310 can be sized such that the space-filler 310 does not come into contact with the chamber interior lateral walls 320. FIG. 3C also illustrates that a separation distance 322 or gap can be maintained between the space-filler 310 and each of the chamber interior lateral walls 320 even when the space-filler 310 is enlarged in response to the external energy 318 directed at the space-filler 310. This ensures that the enlarged space-filler 310 does not expand the peripheral fluid chamber 108 or expand the peripheral fluid chamber 108 to an extent that would cancel out the effects of the enlarged space-filler 310 on reducing the volume of the peripheral fluid chamber 108. Moreover, an anterior-to-posterior height of the space-filler 310 can be significantly less than the chamber height 302 such that the enlarged space-filler 310 does not come into contact with the chamber anterior wall 314.

In some embodiments, the external energy 318 can be light energy. More specifically, the external energy 318 can be laser light. The external energy 318 can be a burst of laser light.

In certain embodiments, the laser light can have a wavelength between about 488 nm to about 650 nm. For example, the laser light can be green laser light. The green laser light can have a wavelength of between about 520 nm to about 570 nm. In one example, embodiment, the external energy 318 can be green laser light having a wavelength of about 532 nm.

For example, the laser light can be laser light emitted by an ophthalmic laser. For example, the laser light can be laser light emitted by a retinal coagulation laser.

In certain embodiments, the laser light can be emitted by a neodymium-doped yttrium aluminum garnet (Nd:YAG) laser. As a more specific example, the laser light can be a pulsed Nd:YAG laser operating in a Q-switching mode and frequency doubled to generate laser light at 532 nm.

In other embodiments, the laser light can be emitted by a femtosecond laser or an infrared or near infrared laser. For example, the laser light emitted by such lasers can have a wavelength of between about 1030 nm and 1064 nm.

As will be discussed in more detail in the following sections, when the external energy 318 is light energy, energy absorbing constituents 404 (see FIG. 4A) within the composite material 400 can absorb or otherwise capture the light energy and convert the light energy into thermal energy and transfer the thermal energy to expandable components 406 (see FIGS. 4A and 4B) within the composite material 400 to expand the expandable components 406.

As previously discussed, in some embodiments about 15 nL of the fluid can flow from the peripheral fluid chamber 108 into the optic fluid chamber 106 (through the fluid channel 110) in response to expansion of one of the space-fillers 310. In these and other embodiments, the base power of the optic portion 102 can be configured to change by about +0.1 D in response to pulses of the external energy 318 directed at one of the space-fillers 310.

FIG. 3D illustrates that an external energy 318 can be directed at a second peripheral component 140 of the adjustable IOL 100 to induce a shape change in the second peripheral component 140.

The second peripheral component 140 can be made of the composite material 400. The second peripheral component 140 can be positioned within the peripheral fluid chamber 108.

In some embodiments, the composite material 400 used to make the second peripheral component 140 can be cured within the peripheral fluid chamber 108 along with the rest of the material used to construct the peripheral fluid chamber 108. In these embodiments, the second peripheral component 140 can be cured in place within the peripheral fluid chamber 108.

In other embodiments, the second peripheral component 140 can be adhered to the interior walls or surfaces of the peripheral fluid chamber 108 using an adhesive. The adhesive can be cured to secure the second peripheral component 140 to the interior walls or surfaces of the peripheral fluid chamber 108.

The second peripheral component 140 can be configured as a chamber expander 312. In some embodiments, the chamber expander 312 can be implemented as an expandable column extending from the chamber anterior wall 314 to the chamber posterior wall 316 (see, e.g., FIG. 3B). Although the figures illustrate the chamber expanders 312 shaped as substantially elongate cylinders, it is contemplated by this disclosure that the chamber expanders 312 can be substantially shaped as elongate ovoids, elongate ellipsoids, elongate cuboids or other polyhedrons, conics, frustoconics, or a combination thereof.

As a more specific example, the chamber expander 312 can be implemented as an expandable column extending from the chamber anterior wall 314 to the chamber posterior wall 316. Expansion of the expandable column can increase the volume of the peripheral fluid chamber 108 by pushing on one or both of the chamber interior wall 314 and chamber posterior wall 316 to increase the chamber height 302. The base power of the optic portion 102 can be configured to decrease in response to the external energy 318 directed at the expandable column.

As shown in FIG. 3D, the chamber expander 312 can expand in response to a burst of the external energy 318 directed at the chamber expander 312. Expansion of the chamber expander 312 can increase a volume of the peripheral fluid chamber 108 and draw fluid from the optic fluid chamber 106 into the peripheral fluid chamber 108. The base power of the optic portion 102 can be configured to decrease in response to the external energy 318 directed at the chamber expander 312.

The external energy 318 can be the same external energy 318 as previously disclosed. For example, the external energy 318 can be light energy.

FIG. 3D illustrates that the chamber expander 312 can be sized such that the chamber expander 312 does not come into contact with the chamber interior lateral walls 320 (even when expanded). This ensures that the enlarged chamber expander 312 expands the peripheral fluid chamber 108 primarily in an anterior-to-posterior direction and does not put pressure on the radially inner chamber wall 132 (which could then translate into pressure applied to the lateral sides of the optic portion 102, thereby inadvertently affecting the optical power).

As previously discussed, in some embodiments about 15 nL of the fluid can flow from the optic fluid chamber 106 into the peripheral fluid chamber 108 (through the fluid channel 110) in response to pulses of the external energy 318 directed at one of the chamber expanders 312. In these and other embodiments, the base power of the optic portion 102 can be configured to change by about −0.1 D in response to an expansion of one of the chamber expanders 312 caused by the external energy 318 directed at the chamber expander 312.

Although FIGS. 1A, 1B, 2B, and 5 illustrate each of the peripheral fluid chambers 108 (e.g., each of the haptic fluid chambers) comprising both the space-fillers 310 and the chamber expanders 312, it is contemplated by this disclosure and it should be understood by one of ordinary skill in the art that each of the peripheral fluid chambers 108 can also comprise only the space-fillers 310 or only the chamber expanders 312.

One technical problem faced by the applicants is how to provide a clinician or other medical professional the ability to fine tune the optical power of an implanted IOL in both directions (i.e., providing the clinician the ability to increase or decrease the optical power of the implanted IOL post-operatively). One solution discovered by the applicants are the peripheral components disclosed herein including, for example, the space-fillers and chamber expanders made of the composite material. As a more specific example, each peripheral fluid chamber (or haptic fluid chamber) can comprise a plurality of the space-fillers, the chamber expanders, or both the space-fillers and chamber expanders. Each peripheral component can be configured to cause the optic portion of the adjustable IOL to change by about 0.1 D in response to a burst of an external energy directed at the peripheral component.

Figure 4A:
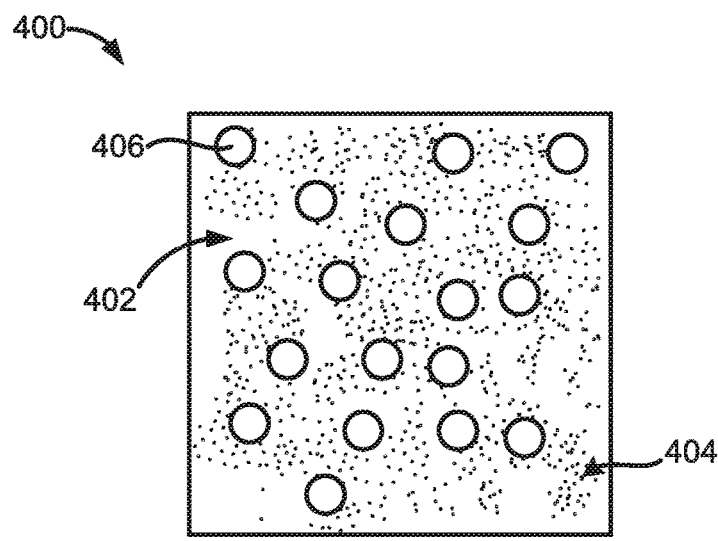
FIG. 4A illustrates a composite material used to make at least part of the adjustable intraocular lens.

FIG. 4A is a graphic representation of a composite material 400 comprising a composite base material 402, an energy absorbing constituent 404, and a plurality of expandable components 406. As previously discussed, at least part of the peripheral portion 103 or components within the peripheral portion 103 can be made of the composite material 400.

The composite base material 402 can be comprised of hydrophobic acrylic materials. For example, the composite base material 402 can be comprised of phenylethyl acrylate (PEA), a phenylethyl methacrylate (PEMA), or a combination thereof.

In one example embodiment, the composite base material 402 can comprise a methacrylate-functional or methacrylic-functional cross-linkable polymer and reactive acrylic monomer diluents including lauryl methacrylate (n-dodecyl methacrylate or SR313) and ADMA. By controlling the amount of lauryl methacrylate (SR313) to ADMA, the overall corresponding hardness (i.e., more ADMA) or softness (i.e., more SR313) of the cured composite material 400 can be controlled. The methacrylate-functional or methacrylic-functional cross-linkable polymer can be made using the cross-linkable polymer precursor formulation.

The cross-linkable polymer precursor formulation can comprise the same copolymer blend used to make the optic portion and the haptics.

The copolymer blend can comprise an alkyl acrylate or methacrylate (e.g., n-butyl acrylate), a fluoro-alkyl (meth)acrylate (e.g., trifluoroethyl methacrylate), and a phenyl-alkyl acrylate (e.g., phenylethyl acrylate). For example, the copolymer blend can comprise n-butyl acrylate in the amount of about 41% to about 45% (wt %), trifluoroethyl methacrylate in the amount of about 20% to about 24% (wt %), and phenylethyl acrylate in the amount of about 28% to about 32% (wt %). The cross-linkable polymer precursor formulation can comprise or be made in part of the copolymer blend, a hydroxyl-functional acrylic monomer (e.g., HEA), and a photoinitiator (e.g., Darocur 4265 or a 50/50 blend of diphenyl(2,4,6-trimethylbenzoyl)-phosphine oxide and 2-hydroxy2-methylpropiophenone).

The composite base material 402 can comprise the methacrylate-functional or methacrylic-functional cross-linkable polymer (as discussed above) in the amount of about 50% to about 65% (e.g., about 55% to about 60%) (wt %), the reactive acrylic monomer diluent lauryl methacrylate (SR313) in the amount of about 32% to about 38% (e.g., about 32.70%) (wt %), the reactive acrylic monomer diluent adamantly methacrylate (ADMA) in the amount of about 5% to about 9% (e.g., about 7.30%) (wt %).

Table 1 below provides an example formulation for the composite material 400:

TABLE 1

| FORMULATION OF COMPOSITE MATERIAL (WT %) | |
|---|---|
| Cross-linkable polymer (in two steps from precursor formulation, as described above) | 1.47% 2-hydroxyethyl acrylate (HEA) <br> 1.96% Darocur 4265 (photoinitiator) <br> 43.49% n-butylacrylate (nBA) <br> 30.21% 2-phenylethylacrylate (PEA) <br> 22.87% 2,2,2-trifluoroethylmethacrylate (TFEMA) |
| Composite base material | 60.00% cross-linkable polymer <br> 32.70% lauryl methacrylate (SR313) <br> 7.30% 1-adamantyl methacrylate (ADMA) |
| Composite base material with red energy absorbing colorant | 99.50% composite base material <br> 0.50% Disperse Red 1 dye |
| Composite base material with black energy absorbing colorant | 99.95% composite base material <br> 0.05% graphitized mesoporous carbon black |
| Final formulation of composite material | 87.70% composite base material with red or black energy absorbing colorant <br> 10.00% expandable microspheres <br> 1.00% Luperox peroxide (thermal initiator) <br> 1.30% Omnirad 2022 |

The composite material 400 can be made in several operations. The first operation can comprise preparing an uncolored composite base material 402. The second operation can comprise mixing the composite base material 402 with an energy absorbing constituent 404, expandable components 406, and initiators such as one or more photoinitiators, thermal initiators, or a combination thereof. The third operation can comprise placing the uncured composite material 400 into a desired location within the peripheral portion 103 (e.g., the peripheral fluid chambers 108 and/or the haptic(s) 104), and curing the composite material 400 in place.

For example, the uncolored composite base material 402 can be mixed with an energy absorbing constituent 404 such as a dye (e.g., Disperse Red 1 dye) or pigment (graphitized carbon black). The energy absorbing constituent 404 will be discussed in more detail below.

In some embodiments, the expandable components 406 can make up about 5.0% to about 15.0% by weight of a final formulation of the composite material 400. More specifically, the expandable components 406 can make up about 8.0% to about 12.0% (e.g., about 10.0%) by weight of a final formulation (see Table 1) of the composite material 400. In these and other embodiments, the energy absorbing constituent 404 can make up about 0.044% to about 0.44% (or about 0.55%) by weight of the final formulation of the composite material 400.

The photoinitiator can be Omnirad 2022 (bis(2,4,6-trimethylbenzoyl)phenyl-phosphineoxide/2-hydroxy-2-methyl-1-phenyl-propan-1-one). The photoinitiator can make up about 1.30% by weight of a final formulation of the composite material 400 (see, e.g., Table 1). In addition, the composite material 400 can also comprise a thermal initiator. The thermal initiator can make up about 1.00% by weight of a final formulation of the composite material 400 (see, e.g., Table 1). In some embodiments, the thermal initiator can be a dialkyl peroxide such as Luperox® peroxide. In other embodiments, the thermal initiator can be Perkadox.

In some embodiments, the energy absorbing constituent (e.g., dye or pigment) can be positioned or located adjacent to the uncolored composite base material 402. In this embodiment, the energy absorbing constituent 404 can absorb the external energy 318 (e.g., laser energy), convert the energy to heat, and conduct the energy to the composite base material 402 to expand the composite base material 402. One added benefit of this approach is that the energy absorbing constituent 404 can be made more discrete and an easier target for a clinician or surgeon to hit with a laser or other external energy 318.

Figure 4B:
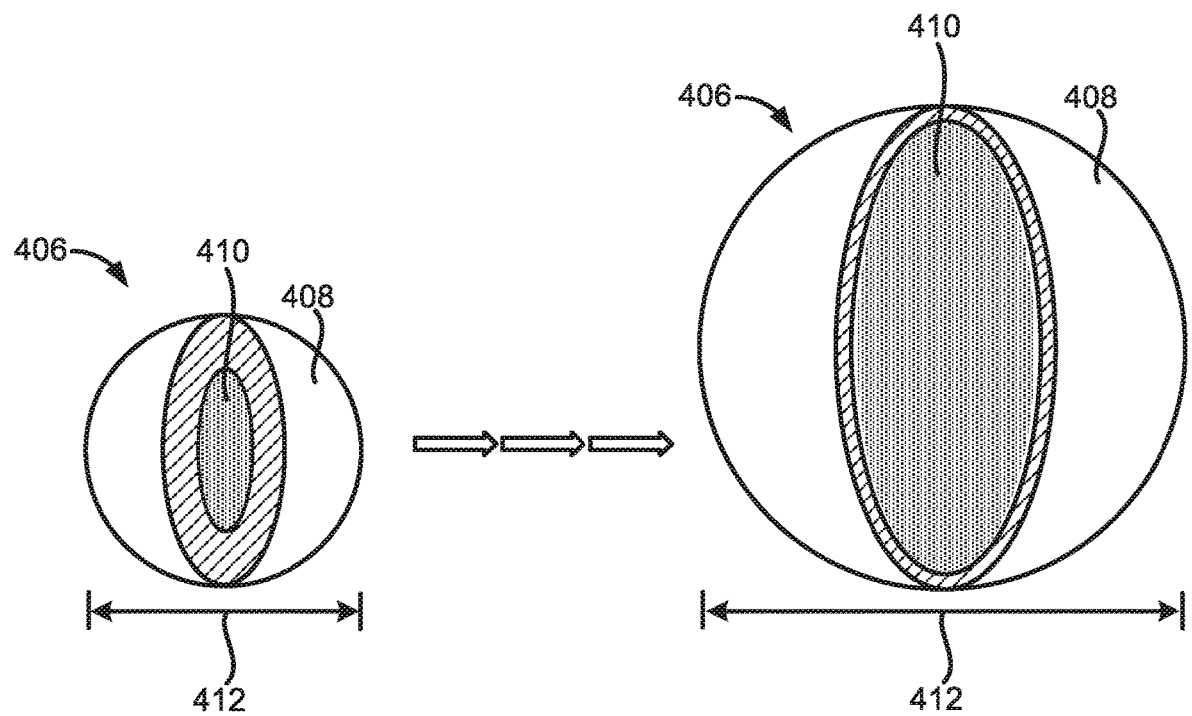
FIG. 4B illustrates one embodiment of an expandable component of the adjustable intraocular lens.

FIG. 4B illustrates that the expandable components 406 can be expandable microspheres comprising an expandable thermoplastic shell 408 and a blowing agent 410 contained within the expandable thermoplastic shell 408. The microspheres can be configured to expand such that a diameter 412 of at least one of the microspheres can increase about 2× the original diameter. In other embodiments, the microspheres can be configured to expand such that the diameter 412 of at least one of the microspheres can increase about 4× or four times the original diameter. In further embodiments, the microspheres can be configured to expand such that the diameter 412 of at least one of the microspheres can increase between about 2× and about 4× (or about 3.5×) the original diameter. For example, the microspheres can have a diameter 412 of about 12 μm at the outset. In response to an external energy applied or directed at the composite material 400 or in response to energy transferred or transmitted to the microspheres, the diameter 412 of the microspheres can increase to about 40 μm.

The volume of at least one of the microspheres can be configured to expand between about ten times (10×) to about 50 times (50×) in response to the external energy applied or directed at the composite material 400 or in response to energy transferred or transmitted to the microspheres.

In some embodiments, the blowing agent 410 can be an expandable fluid, such as an expandable gas. More specifically, the blowing agent 410 can be a branched-chain hydrocarbon. For example, the blowing agent 410 can be isopentane. In other embodiments, the blowing agent 410 can be or comprise cyclopentane, pentane, or a mixture of cyclopentane, pentane, and isopentane.

The expandable components 406 can comprise differing amounts of the blowing agent 410. For example, some expandable components 406 can comprise more or a greater amount of the blowing agent (e.g., more expandable gas) to allow such expandable components 406 to expand more, resulting in greater expansion of the composite material 400 comprising such expandable components 406.

FIG. 4B illustrates that each of the expandable components 406 can comprise a thermoplastic shell 408. FIG. 4B also illustrates that a thickness of the thermoplastic shell 408 can change as the expandable component 406 increases in size. More specifically, the thickness of the thermoplastic shell 408 can decrease as the expandable component 406 increases in size. For example, when the expandable components 406 are expandable microspheres, the thickness of the thermoplastic shell 408 (i.e., its thickness in a radial direction) can decrease as the diameter 412 of the expandable microsphere increases.

For example, as previously discussed, at least one of the expandable microspheres can have a diameter 412 of about 12 µm at the outset. In this embodiment, the thermoplastic shell 408 of the expandable microsphere can have a shell thickness of about 2.0 µm. In response to an external energy applied or directed at the composite material 400 or in response to energy transferred or transmitted to the microsphere, the diameter 412 of the microsphere can increase to about 40 µm (and the volume expand between about 10× and 50×) and the shell thickness of the microsphere can decrease to about 0.1 µm.

Although FIGS. 4A and 4B illustrate the expandable components 406 as spheres or microspheres, it is contemplated by this disclosure that the expandable components 406 can be substantially shaped as ovoids, ellipsoids, cuboids or other polyhedrons, or a combination thereof.

In some embodiments, the thermoplastic shell 408 can be made in part of nitriles or acrylonitrile copolymers. For example, the thermoplastic shell 408 can be made in part of acrylonitrile, styrene, butadiene, methyl acrylate, or a combination thereof.

As previously discussed, the expandable components 406 can make up between about 8.0% to about 12% by weight of a final formulation of the composite material 400. The expandable components 406 can make up about 10% by weight of a final formulation of the composite material 400.

The expandable components 406 can be dispersed or otherwise distributed within the composite base material 402 making up the bulk of the composite material 400. The composite base material 402 can serve as a matrix for holding or carrying the expandable components 406. The composite material 400 can expand in response to an expansion of the expandable components 406 (e.g., the thermoplastic microspheres). For example, a volume of the composite material 400 can increase in response to the expansion of the expandable components 406.

The composite material 400 also comprises an energy absorbing constituent 404. In some embodiments, the energy absorbing constituent 404 can be an energy absorbing colorant.

In certain embodiments, the energy absorbing colorant can be an energy absorbing dye. For example, the energy absorbing dye can be an azo dye. In some embodiments, the azo dye can be a red azo dye such as Disperse Red 1 dye. In other embodiments, the azo dye can be an orange azo dye such as Disperse Orange dye (e.g., Disperse Orange 1), a yellow azo dye such as Disperse Yellow dye (e.g., Disperse Yellow 1), a blue azo dye such as Disperse Blue dye (e.g., Disperse Blue 1), or a combination thereof.

In additional embodiments, the energy absorbing colorant can be or comprise a pigment. For example, the energy absorbing colorant can be or comprise graphitized carbon black as the pigment.

Similar to the expandable components 406, the energy absorbing constituent 404 can be dispersed or otherwise distributed within the composite base material 402 making up the bulk of the composite material 400. The composite base material 402 can serve as a matrix for holding or carrying the expandable components 406 and the energy absorbing constituent 404.

As previously discussed, the energy absorbing constituent 404 can make up between about 0.025% to about 1.0% (or, more specifically, about 0.045% to about 0.45%) by weight of a final formulation of the composite material 400. For example, when the energy absorbing constituent 404 is a dye (e.g., an azo dye such as Disperse Red 1), the energy absorbing constituent 404 can make up about between about 0.45% to about 1.0% by weight of a final formulation of the composite material 400. When the energy absorbing constituent 404 is graphitized carbon black or other types of pigments, the energy absorbing constituent 404 can make up about 0.025% to about 0.045% by weight of a final formulation of the composite material 400.

The energy absorbing constituent 404 (e.g., azo dye, graphitized carbon black, or a combination thereof) can absorb or capture an external energy applied or directed at the composite material 400. The energy absorbing constituent 404 can absorb or capture the external energy and then transform or transfer the energy into thermal energy or heat to the expandable components 406.

The thermoplastic shell 408 can soften and begin to flow as thermal energy is transferred or transmitted to the expandable components 406. The thermoplastic shell 408 of the expandable components 406 can then begin to thin or reduce in thickness in response to the thermal energy transferred or transmitted to the expandable components 406. As the thermoplastic shell 408 begins to soften and reduce in thickness, the blowing agent 410 within the expandable components 406 can expand. The blowing agent 410 can also expand in response to the thermal energy or heat transferred or transmitted to the expandable components 406. Expansion of the blowing agents 410 can cause the expandable components 406 (e.g., the thermoplastic microspheres) to expand or increase in volume. This ultimately causes the composite material 400 to expand or increase in volume.

The composite material 400 can expand or increase in size in an isotropic manner such that the composite material 400 expands in all directions. Such isotropic expansion can be harnessed to produce expansion or material displacement in specific directions by placing or positioning the composite material 400 at specific locations within the peripheral fluid chambers 108 along the haptic(s) 104 or optic portion 102 of the adjustable IOL 100.

As will be discussed in more detail in the following sections, in some embodiments, the external energy can be light energy and the energy absorbing constituent 404 can absorb or capture the light energy directed at the composite material 400 and transform or transfer the light energy into thermal energy or heat to the expandable components 406. The blowing agent 410 within the expandable components 406 can expand or become energized in response to the thermal energy or heat. The expandable components 406 and, ultimately, the composite material 400 can expand or increase in volume in response to this light energy directed at the composite material 400.

The shape change (e.g., increase in volume) undertaken by the expandable components 406 can be a persistent or a substantially permanent change. A persistent or substantially permanent change can mean that the expandable components 406 do not substantially revert back to its original shape or size after the shape change (e.g., after an increase in volume) has occurred. As a result, any change in the size or volume of the composite material 400 caused by a change in the size or volume of the expandable components 406 is also persistent or substantially permanent. As will be discussed in more detail in the following sections, this means that any structural changes made to the adjustable IOL 100 as a result of external energy or stimulus applied or otherwise directed at the composite material 400 embedded or integrated within the adjustable IOL 100 can persist or remain substantially permanent.

The thermoplastic shells 408 of the expandable components 406 can harden, once again, when the external energy is no longer directed or applied to the composite material 400. For example, the thermoplastic shells 408 may again harden when the temperature within a vicinity of the expandable components 406 falls below a certain threshold. For example, the thermoplastic shells 408 of the expandable microspheres can harden when light energy is no longer directed at the composite material 400. After the thermoplastic shells 408 harden, the expandable components 406 are locked into their new size and expanded configuration.

When the energy absorbing constituent 404 is an energy absorbing colorant, such as a dye or graphitized carbon, the color of at least part of the composite material 400 can take on the color of the energy absorbing colorant. For example, when the energy absorbing constituent 404 is an azo dye such as Disperse Red 1 having a red color, at least a portion of the composite material 400 comprising the energy absorbing constituent 404 can be colored red. Moreover, when the energy absorbing constituent 404 is graphitized carbon having a black color, at least a portion of the composite material 400 comprising the energy absorbing constituent 404 can be colored black. Although two colors (e.g., red and black) are mentioned in this disclosure, it is contemplated by this disclosure and it should be understood by one of ordinary skill in the art that energy absorbing colorant of other types of colors can also be used such as energy absorbing yellow, orange, or blue dyes or materials.

The color of the energy absorbing colorant can be visually perceptible to a clinician or another medical professional when at least part of the adjustable IOL 100 is made of the composite material 400 comprising the energy absorbing colorant. The color of the energy absorbing colorant can be visually perceptible to a clinician or another medical professional when the adjustable IOL 100 is implanted within an eye of a patient. For example, the composite material 400 can comprise Disperse Red 1 serving as the energy absorbing colorant. In this example, at least part of the adjustable IOL 100 can appear red to the clinician or another medical professional when the adjustable IOL 100 is implanted within the eye of a patient.

The color of the energy absorbing colorant can allow the clinician or another medical professional to detect or determine the location or position of the composite material 400 within the adjustable IOL 100. The color of the energy absorbing colorant can also allow the clinician or another medical professional to determine where to direct the external energy or stimulus to adjust the adjustable IOL 100.

One technical problem faced by the applicants is how to integrate the composite material into the peripheral portion (e.g., the haptics) of the adjustable IOL such that the composite material would adhere to the material used to make the rest of the adjustable IOL and remain substantially fixed at certain locations within the peripheral portion. One solution discovered by the applicants and disclosed herein is the unique composition of the composite material 400 which incorporates the same copolymer blend used to make the rest of the lens. By designing the adjustable IOL in this manner, the composite material 400 can be compatible with the rest of the material used to construct the peripheral portion and remains substantially fixed at its location without migrating or shifting.

Another technical problem faced by the applicants is how to ensure that any adjustments made to the adjustable IOL persist long after the adjustment procedure. One solution discovered by the applicants and disclosed herein is to induce an expansion of a composite material made in part of expandable microspheres comprising a blowing agent contained within thermoplastic shells. The thermoplastic shells can soften (and the thickness of the thermoplastic shells can decrease) in response to an external energy directed or applied at the composite material (which can result in heat or thermal energy being transferred or transmitted to the expandable microspheres). The blowing agent within the thermoplastic shells can expand as the thermoplastic shells soften. Expansion of the blowing agent can expand the microspheres, which can, in turn, expand the composite base material serving as the bulk of the composite material. The expandable microspheres can retain their new enlarged or expanded configuration even after the external energy is no longer applied to the composite material.

Moreover, the energy absorbing constituent of the composite material 400 can capture or absorb a relatively harmless external energy or stimulus directed at the composite material and transform or transfer the external energy into thermal energy which can then cause the thermoplastic microspheres to expand. By designing the adjustable IOL 100 in this manner, a burst of relatively harmless energy or stimulus (e.g., light energy) can be used to induce a persistent change in the shape or size of at least part of the adjustable IOL 100. This persistent change in the shape or size of the adjustable IOL 100 can have a continuing effect on an optical parameter of the lens including, for example, its base power.

Figure 5:
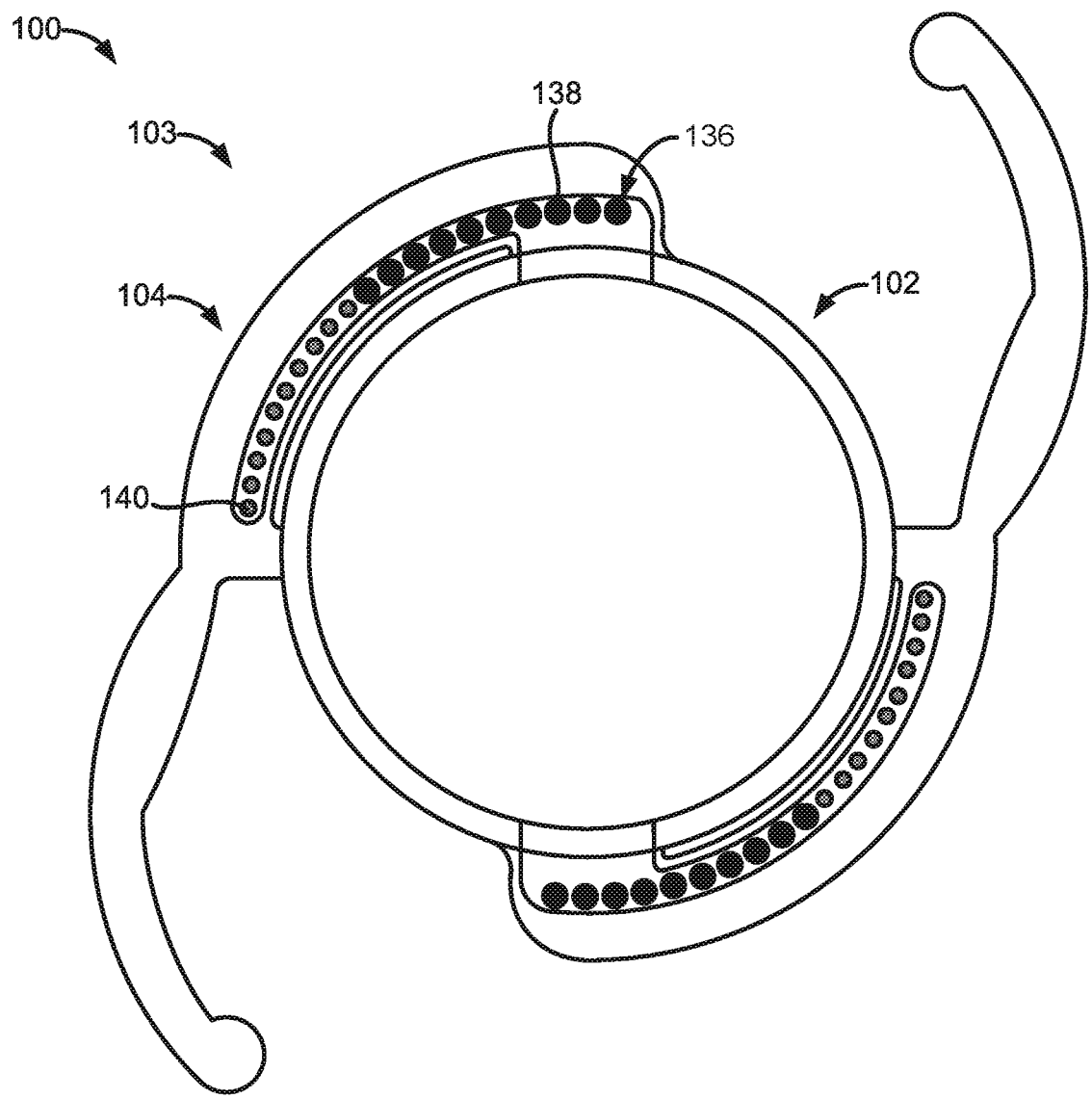
FIG. 5 illustrates a top plan view of another embodiment of the adjustable IOL with part of the anterior portion of the adjustable IOL removed to better illustrate components within the IOL.

FIG. 5 illustrates a top plan view of another embodiment of the adjustable static-focus IOL 100 with part of the anterior portion of the adjustable IOL 100 removed to better illustrate components within the IOL. As shown in FIG. 5, the first peripheral components 138 can be made of a first composite material comprising a first energy absorbing constituent having a first color and the second peripheral components 140 can be made of a second composite material comprising a second energy absorbing constituent having a second color different from the first color. This difference in color can be visually perceptible to a clinician or another medical professional and can allow the clinician or other medical professional to visually differentiate between the two types of peripheral components 136.

For example, the first energy absorbing constituent can be an energy absorbing dye. As a more specific example, the energy absorbing dye can be an azo dye such as a red azo dye (e.g., Disperse Red 1 dye). In this example, the second energy absorbing constituent can be another energy absorbing dye such as a yellow azo dye or another lighter-colored dye.

In other examples, the first energy absorbing constituent can be or comprise a pigment such as graphitized carbon black (which exhibits a black color). In these examples, the second energy absorbing constituent can be an energy absorbing dye (e.g., a red azo dye).

In additional examples, the second energy absorbing constituent can be or comprise a pigment such as graphitized carbon black (which exhibits a black color). In these examples, the first energy absorbing constituent can be an energy absorbing dye (e.g., a red azo dye).

In other embodiments, the first composite material and the second composite material can be made in part of the same energy absorbing constituents or colorants but comprise different amounts or weight percentages of such constituents or colorants.

In certain embodiments, the first peripheral component 138 made of the first composite material (and having a first color) can expand or change shape in response to a first type of external energy (e.g., light energy between 520 nm to 540 nm) directed at the first composite material and the second peripheral component 140 made of the second composite material (and having a second color different from the first color) can expand in response to a second type of external energy (e.g., light energy between 600 nm and 650 nm) directed at the second composite material.

By designing the adjustable IOL 100 in this manner, a clinician or another medical professional can direct external energy or stimulus at different target sites along the peripheral portion 103 using the different colors of the composite materials as guides or markers. Moreover, the different colored composite materials can also serve as indicators or visual cues as to where to direct the external energy or stimulus to cause certain changes in the base power of the optic portion 102.

For example, the adjustable IOL 100 can be configured such that a base power of the adjustable IOL 100 can be adjusted in a first manner (e.g., the base power can be increased) by directing or otherwise applying an external energy at a first peripheral component 138 made of the first composite material (having a first color). The base power of the adjustable IOL 100 can also be adjusted in a second manner (e.g., the base power can be decreased) by directing or otherwise applying additional bursts or pulses of the external energy at a second peripheral component 140 made of a second composite material (having a second color different from the first color).

Figure 6:
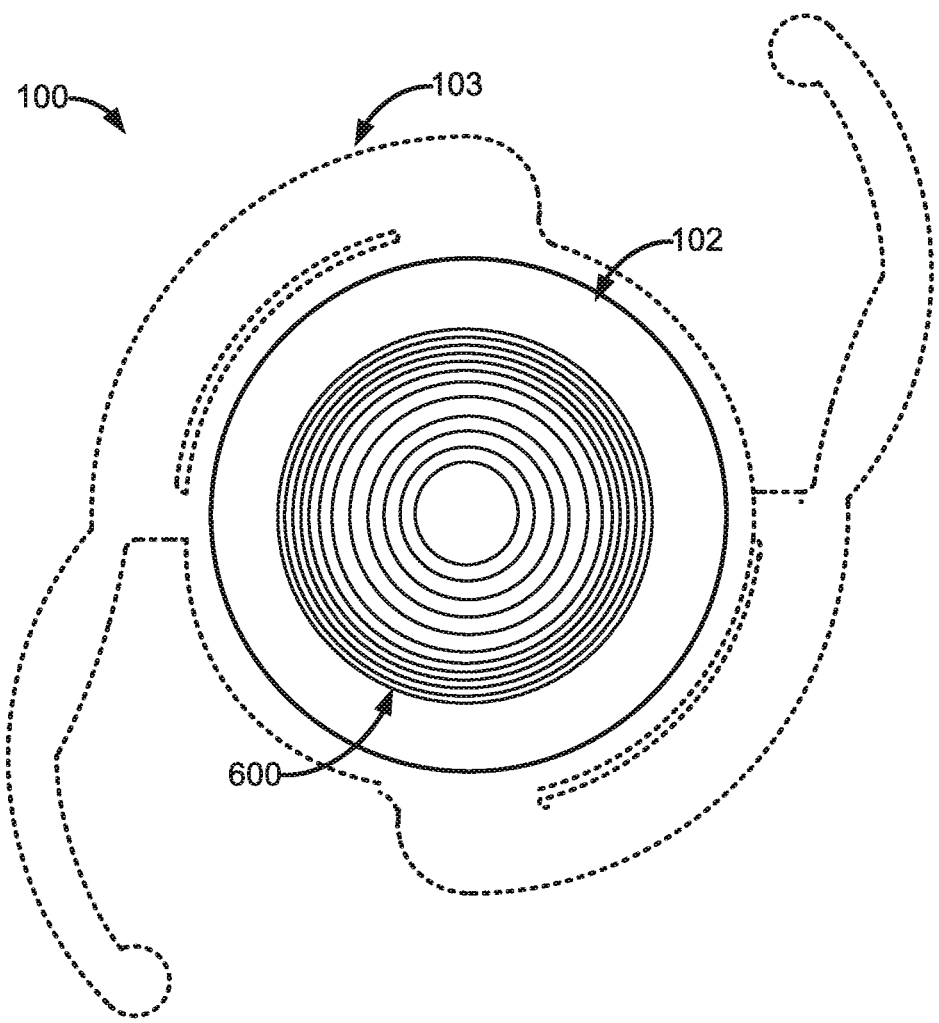
FIG. 6 illustrates a top plan view of the adjustable IOL with a light splitting lens surface profile.

FIG. 6 illustrates a top plan view of another embodiment of the adjustable IOL 100 with an optic portion 102 comprising a light splitting lens surface profile 600. The peripheral portion 103 of the adjustable IOL 100 is shown in broken lines to emphasize the optic portion 102.

One technical problem faced by the applicants is how to design a fluid-filled IOL that can be used by patients seeking different types of vision support (e.g., near vision, intermediate vision, distance vision, etc.). One solution discovered by the applicants is the adjustable IOL disclosed herein where different lens surface profiles, both rotationally symmetric as well as in toric profiles so as to correct for astigmatism, can be defined on an external optical surface (e.g., an anterior optical surface) of the optic portion allowing for the same adjustable IOL structure to be adapted as an adjustable monofocal IOL, an adjustable bifocal IOL, an adjustable trifocal IOL, or an adjustable EDOF IOL, in both toric and non-toric shapes.

As shown in FIG. 6, the optic portion 102 of the adjustable IOL 100 can comprise a light splitting lens surface profile 600 defined on a lens surface of the optic portion 102. In some embodiments, the light splitting lens surface profile 600 can comprise a central diffractive area or structure comprising a plurality of diffractive zones or steps. In these and other embodiments, the widths of the diffractive zones can decrease in a radially outward manner such that zone widths at a periphery of the lens are smaller than zone widths near a central portion of the lens.

The light splitting lens surface profile 600 can split light into multiple foci or focal points. In these embodiments, the adjustable IOL 100 can be considered an adjustable multifocal IOL or a non-accommodating fluid-adjustable multifocal IOL. Even though the light splitting lens surface profile 600 can split light into multiple foci or focal points, each such focal point is static and the fluid-adjustable multifocal IOL is considered non-accommodating.

In some embodiments, the light splitting lens surface profile 600 can be configured to split light into two focal points (e.g., allowing for near and distant vision). In these embodiments, the adjustable IOL 100 can be considered an adjustable bifocal IOL or a non-accommodating fluid-adjustable bifocal IOL. In these embodiments, even though the light splitting lens surface profile 600 can split light into two focal points, each such focal point is static and the fluid-adjustable bifocal IOL is considered non-accommodating.

The light splitting lens surface profile 600 can also be configured to split light into three focal points (e.g., allowing for near, intermediate, and distant vision). In these embodiments, the adjustable IOL 100 can be considered an adjustable trifocal IOL or a non-accommodating fluid-adjustable trifocal IOL.

In other embodiments not shown in FIG. 6, the optic portion 102 of the adjustable IOL 100 can have a uniformly curved (e.g., a spherical) lens surface or an aspherical lens surface providing focusing power for a single distance. In these embodiments, the adjustable IOL 100 can be considered an adjustable monofocal IOL or a non-accommodating fluid-adjustable monofocal IOL.

In additional embodiments not shown in FIG. 6, the optic portion 102 of the adjustable IOL 100 can have a lens surface profile or pattern configured to provide an extended depth of focus or a single elongated focal point. In these embodiments, the adjustable IOL 100 can be considered an adjustable extended depth of focus (EDOF) IOL or a non-accommodating fluid-adjustable EDOF IOL.

It is contemplated by this disclosure that the unique peripheral portion 103 disclosed herein can be compatible with optic portions 102 comprising a variety of lens surface profiles. Thus, directing external energy (e.g., laser light) at peripheral component(s) 136 made of the composite material 400 in the peripheral portion 103 can adjust the focusing power(s) or focusing length(s) provided by such lens surface profiles.

Any of the adjustable monofocal IOL, the adjustable multifocal IOL, and the adjustable EDOF IOL can comprise a toric lens profile.

Figure 7:
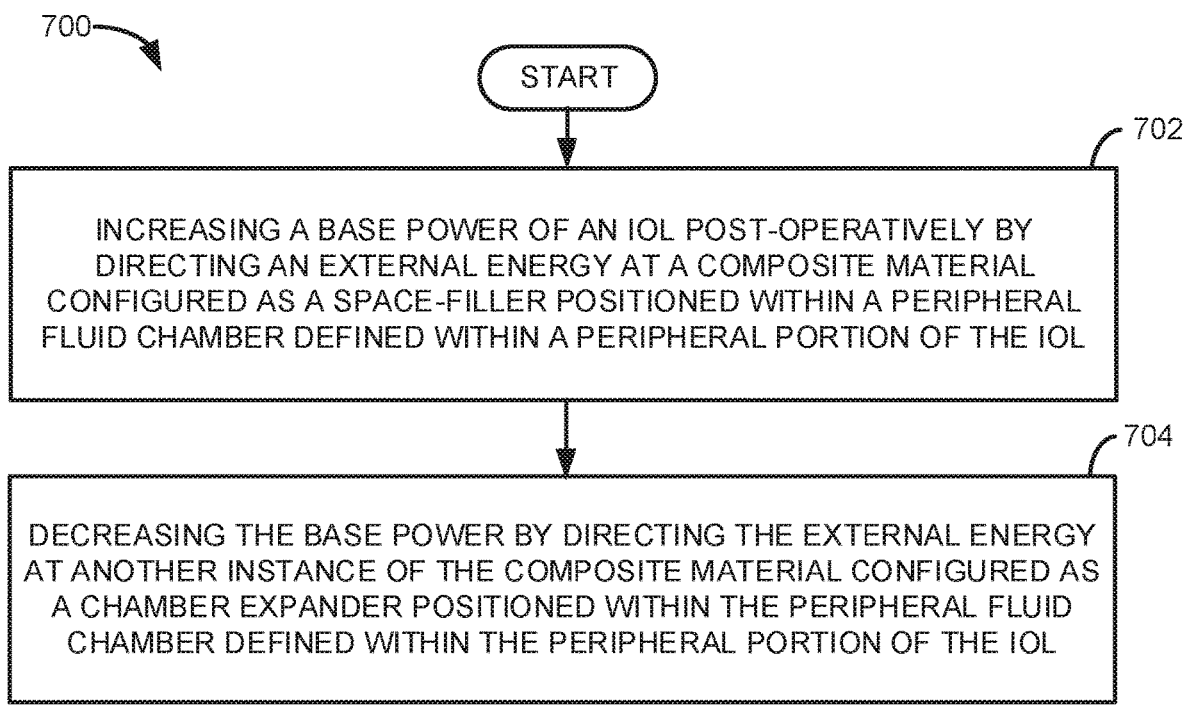
FIG. 7 is one embodiment of a method of adjusting an IOL post-operatively.

FIG. 7 is one embodiment of a method 700 of adjusting an IOL 100 post operatively. The method 700 can comprise increasing a base power of an IOL 100 post-operatively by directing an external energy 318 at a composite material 400 configured as a space-filler 310 positioned within a peripheral fluid chamber 108 defined within a peripheral portion 103 of the IOL 100 in operation 702. The method 700 can also comprise decreasing the base power by directing the external energy 318 at another instance of the composite material 400 configured as a chamber expander 312 positioned within the peripheral fluid chamber 108 in operation 704.

Figure 8:
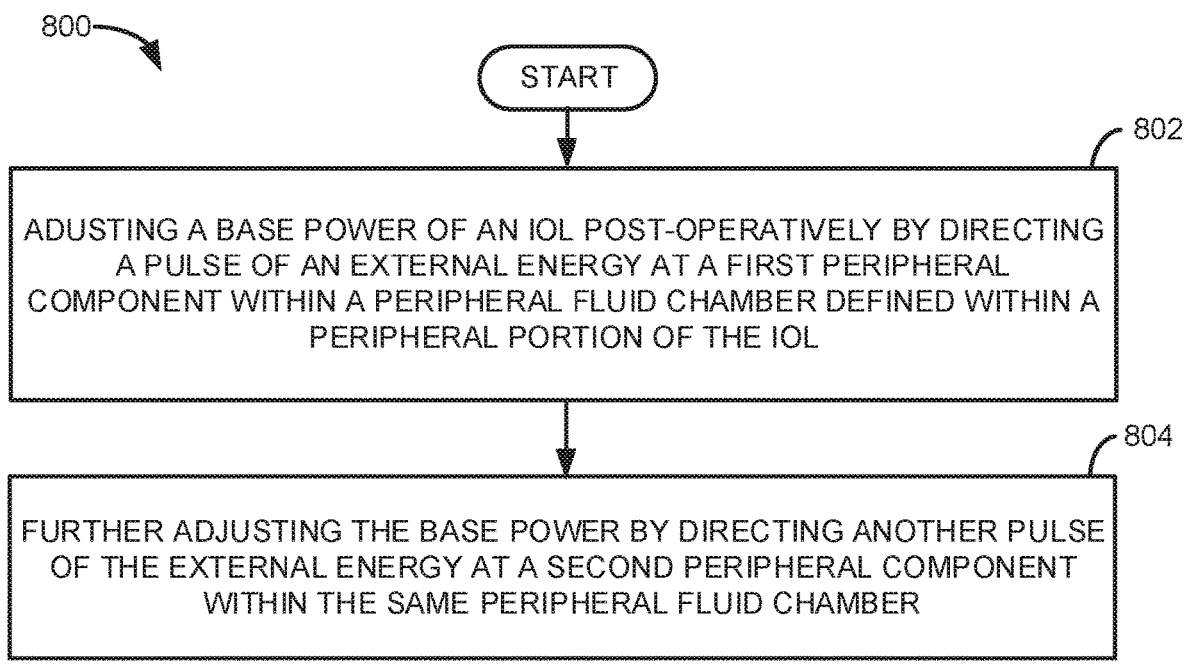
FIG. 8 is another embodiment of a method of adjusting an IOL post-operatively.

FIG. 8 is another embodiment of a method 800 of adjusting an IOL 100 post-operatively. The method 800 can comprise adjusting a base power of the IOL 100 by directing pulses of an external energy 318 at a first peripheral component 138 within a peripheral fluid chamber 108 defined within a peripheral portion 103 of the IOL 100 in operation 802. The method 800 can also comprise further adjusting the base power by directing additional pulses of the external energy 318 at a second peripheral component 140 within the same peripheral fluid chamber 108 in operation 804.

For example, the first peripheral component 138 can be a space-filler 310 and directing the external energy 318 at the space-filler 310 can expand the space-filler 310 and decrease a volume of the peripheral fluid chamber 108 and displace fluid from the peripheral fluid chamber 108 into the optic fluid chamber 106 (thereby increasing the base power of the optic portion 102). The second peripheral component 140 can be a chamber expander 312 and directing the external energy 318 at the chamber expander 312 can expand the chamber expander 312 and increase the volume of the peripheral fluid chamber 108 and draw fluid from the optic fluid chamber 106 into the peripheral fluid chamber 108 (thereby decreasing the base power of the optic portion 102).

Alternatively, the external energy 318 can be directed first at the chamber expander 312 to decrease the base power of the optic portion 102 and then the external energy 318 can be directed subsequently at the space-filler 310 to increase the base power of the optic portion 102.

Figure 9:
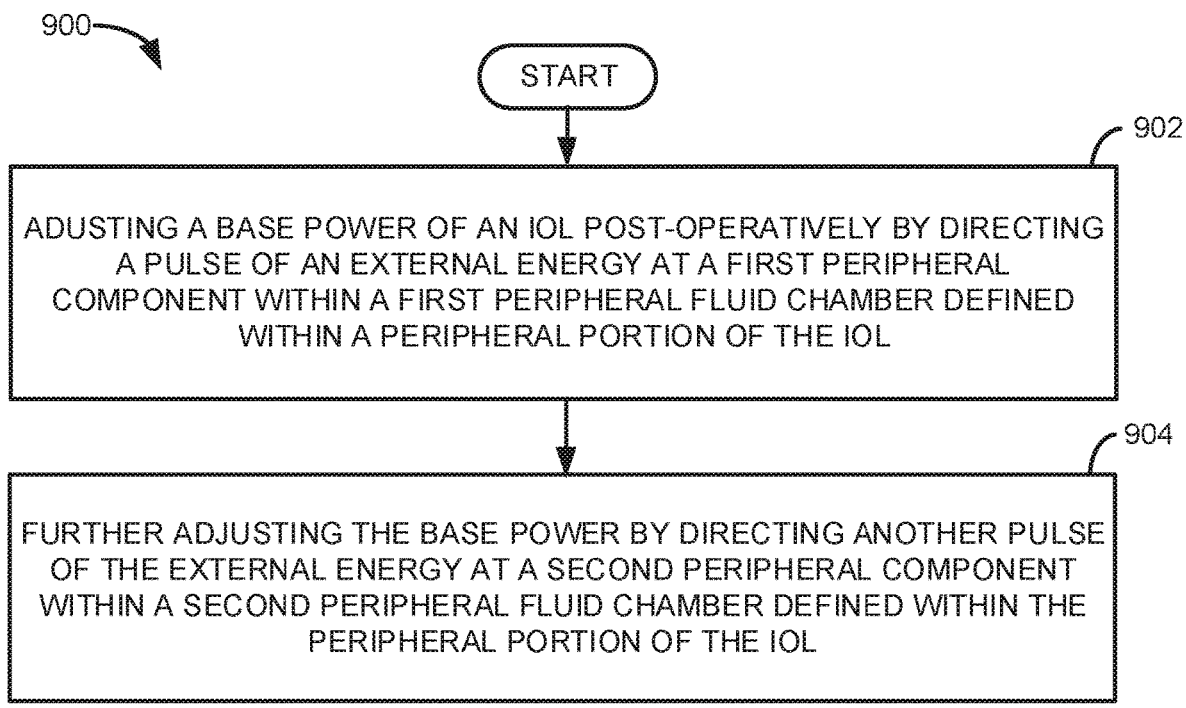
FIG. 9 is yet another embodiment of a method of adjusting an IOL post-operatively.

FIG. 9 is yet another embodiment of a method 900 of adjusting an IOL 100 post-operatively. The method 900 can comprise adjusting a base power of the IOL 100 by directing pulses of an external energy at a first peripheral component 138 within a first of the peripheral fluid chambers 108 (e.g., a first haptic fluid chamber) defined within a peripheral portion 103 of the IOL 100 in operation 902. The method 900 can further comprise adjusting the base power of the IOL 100 by directing additional pulses of the external energy at a second peripheral component 140 or another instance of the first peripheral component 138 within a second of the peripheral chambers 108 (e.g., a second haptic fluid chamber) of the peripheral portion 103 of the IOL 100 in operation 904.

The first peripheral component 138 can be a space-filler 310 and directing the external energy 318 at the space-filler 310 can expand the space-filler 310 and decrease a volume of the first peripheral fluid chamber and displace fluid from the first peripheral fluid chamber into the optic fluid chamber 106 (thereby increasing the base power of the optic portion 102). The second peripheral component 140 can be a chamber expander 312 and directing the external energy 318 at the chamber expander 312 can expand the chamber expander 312 and increase the volume of the second peripheral fluid chamber and draw fluid from the optic fluid chamber 106 into the second peripheral fluid chamber (thereby decreasing the base power of the optic portion 102).

In some embodiments, pulses of the external energy 318 can be directed at a chamber expander 312 within the first peripheral fluid chamber to decrease the base power of the optic portion 102 and additional pulses of the external energy 318 can be directed at a space-filler 310 within the second peripheral fluid chamber to increase the base power of the optic portion 102.

Figure 10:
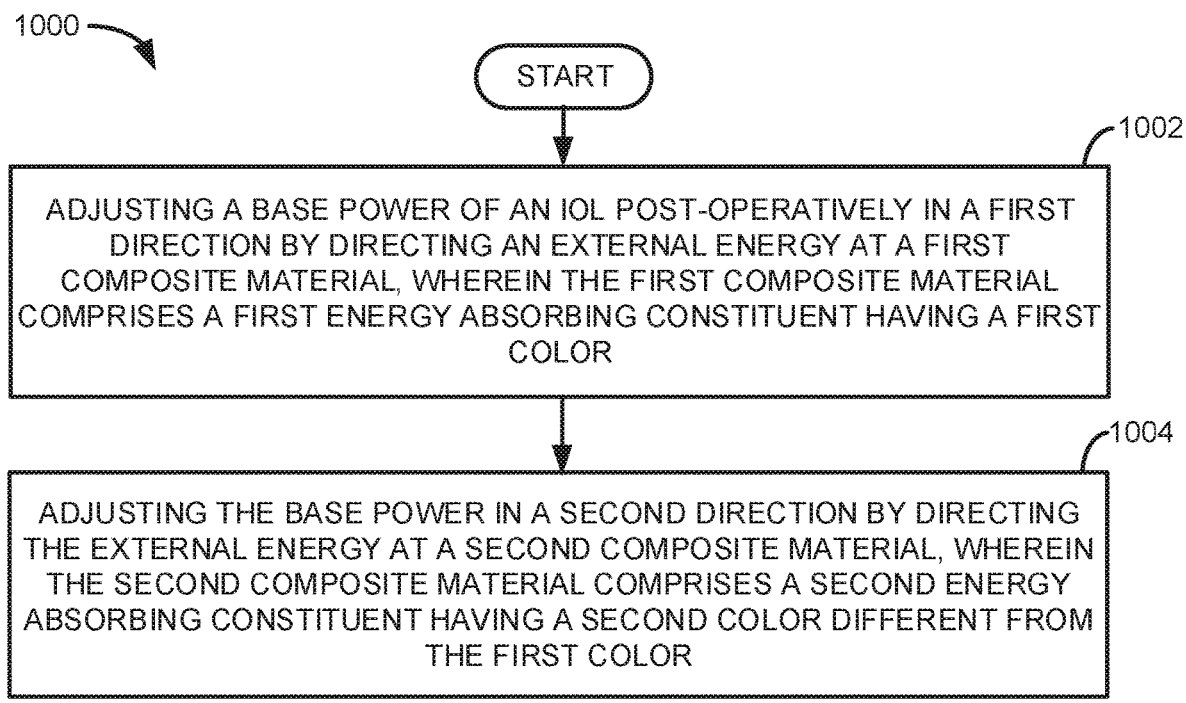
FIG. 10 is an additional embodiment of a method of adjusting an IOL post-operatively.

FIG. 10 is an additional embodiment of a method 1000 of adjusting an IOL 100 post-operatively. The method 1000 can comprise adjusting a base power of the IOL 100 in a first direction by directing an external energy 318 at a first composite material in operation 1002. The first composite material can comprise a first energy absorbing constituent having a first color. The method 1000 can further comprise adjusting the base power of the IOL 100 in a second direction by directing the external energy at a second composite material in operation 1004. The second composite material can comprise a second energy absorbing constituent having a second color different from the first color.

For example, the first composite material can be formed as a space-filler 310. In this example, the first energy absorbing constituent of the first composite material can be an azo dye having a first color (e.g., a red color). Also, in this example, the second composite material can be formed as a chamber expander 312 and the second energy absorbing constituent of the second composite material can be an energy absorbing pigment such as graphitized carbon black or an azo dye having a second color different from the first color (e.g., a blue color or yellow color).

In other embodiments, the first composite material can be formed as a chamber expander 312 and the first energy absorbing constituent of the first composite material can be an azo dye having a first color (e.g., a red color). In these embodiments, the second composite material can be formed as a space-filler 310 and the second energy absorbing constituent of the second composite material can be an energy absorbing pigment such as graphitized carbon black or an azo dye having a second color different from the first color (e.g., a blue color or yellow color).

In one or more of the methods disclosed herein, adjusting the base power of the IOL 100 can comprise adjusting the base power of the optic portion 102 by between about ±0.05 D to about ±0.50 D by directing pulses of the external energy 318 at the composite material 400 to expand the composite material 400. For example, adjusting the base power of the IOL 100 can comprise adjusting the base power of the optic portion 102 by about ±0.10 D by directing pulses of the external energy 318 at the composite material 400 to expand the composite material 400.

For example, the base power of the optic portion 102 can be adjusted by between about ±0.05 D to about ±0.50 D in response to fluid displacement or exchange between the optic fluid chamber 106 and one of the peripheral fluid chambers 108 due to a change in the volume of the peripheral fluid chamber 108 as a result of an expansion of a peripheral component 136 caused by pulses of the external energy 318 directed at the peripheral component 136. As a more specific example, the base power of the optic portion 102 can increase by between about +0.05 D to about +0.50 D in response to fluid entering the optic fluid chamber 106 from one of the peripheral fluid chambers 108 due to a reduction in the volume of the peripheral fluid chamber 108 as a result of an expansion of a first peripheral component 138 caused by pulses of the external energy 318 directed at the first peripheral component 138. As another more specific example, the base power of the optic portion 102 can decrease by between about −0.05 D to about −0.50 D in response to fluid exiting the optic fluid chamber 106 into one of the peripheral fluid chambers 108 due to an increase in the volume of the peripheral fluid chamber 108 as a result of an expansion of a second peripheral component 140 caused by pulses of the external energy 318 directed at the second peripheral component 140.

In one or more of the methods disclosed herein, adjusting the base power of the IOL 100 can comprise adjusting the base power of the IOL 100 in total between about ±1.0 D and about ±2.0 D by directing pulses of the external energy 318 at multiple peripheral components 136.

In one or more of the methods disclosed herein, directing the external energy 318 at the composite material can further comprise directing light energy at the composite material 400. For example, directing the external energy 318 at the composite material 400 can further comprise directing laser light at the composite material 400. As a more specific example, directing the external energy 318 at the composite material 400 can further comprise directing green laser light at the composite material 400.

In one or more of the methods disclosed herein, directing the external energy 318 at the composite material 400 can comprise directing laser light having a wavelength between about 488 nm to about 650 nm at the composite material 400. In other embodiments, directing the external energy 318 at the composite material 400 can further comprise directing laser light having a wavelength between about 946 nm to about 1120 nm at the composite material 400.

One drawback of currently available tunable IOLs (such as light adjustable lens) is that the tuning procedure requires time to take effect, may require multiple visits to a clinician's office, and the clinician must often purchase expensive new equipment to undertake such tuning procedures. One advantage of the static-focus adjustable IOLs 100 disclosed herein is that such static-focus adjustable IOLs 100 allow for post-operative refractive error correction in a matter of seconds rather than hours. This allows patients to provide feedback concerning their refractive error correction almost instantaneously. Moreover, the IOLs 100 disclosed herein can be tuned using commercially available lasers (e.g., 532 nm photocoagulator lasers) that are commonly found in most clinician's offices. Moreover, patients do not need to wear U.V blocking glasses during the healing period and refractive error correction can be undertaken months or even years after the initial implantation procedure.

A number of embodiments have been described. Nevertheless, it will be understood by one of ordinary skill in the art that various changes and modifications can be made to this disclosure without departing from the spirit and scope of the embodiments. Elements of systems, devices, apparatus, and methods shown with any embodiment are exemplary for the specific embodiment and can be used in combination or otherwise on other embodiments within this disclosure. For example, the steps of any methods depicted in the figures or described in this disclosure do not require the particular order or sequential order shown or described to achieve the desired results. In addition, other steps operations may be provided, or steps or operations may be eliminated or omitted from the described methods or processes to achieve the desired results. Moreover, any components or parts of any apparatus or systems described in this disclosure or depicted in the figures may be removed, eliminated, or omitted to achieve the desired results. In addition, certain components or parts of the systems, devices, or apparatus shown or described herein have been omitted for the sake of succinctness and clarity.

Accordingly, other embodiments are within the scope of the following claims and the specification and/or drawings may be regarded in an illustrative rather than a restrictive sense.

Each of the individual variations or embodiments described and illustrated herein has discrete components and features which may be readily separated from or combined with the features of any of the other variations or embodiments. Modifications may be made to adapt a particular situation, material, composition of matter, process, process act(s) or step(s) to the objective(s), spirit or scope of the present invention.

Methods recited herein may be carried out in any order of the recited events that is logically possible, as well as the recited order of events. Moreover, additional steps or operations may be provided or steps or operations may be eliminated to achieve the desired result.

Furthermore, where a range of values is provided, every intervening value between the upper and lower limit of that range and any other stated or intervening value in that stated range is encompassed within the invention. Also, any optional feature of the inventive variations described may be set forth and claimed independently, or in combination with any one or more of the features described herein. For example, a description of a range from 1 to 5 should be considered to have disclosed subranges such as from 1 to 3, from 1 to 4, from 2 to 4, from 2 to 5, from 3 to 5, etc. as well as individual numbers within that range, for example 1.5, 2.5, etc. and any whole or partial increments therebetween.

All existing subject matter mentioned herein (e.g., publications, patents, patent applications) is incorporated by reference herein in its entirety except insofar as the subject matter may conflict with that of the present invention (in which case what is present herein shall prevail). The referenced items are provided solely for their disclosure prior to the filing date of the present application. Nothing herein is to be construed as an admission that the present invention is not entitled to antedate such material by virtue of prior invention.

Reference to a singular item, includes the possibility that there are plural of the same items present. More specifically, as used herein and in the appended claims, the singular forms "a," "an," "said" and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation. Unless defined otherwise, all technical and scientific terms used herein have the same meaning as commonly understood by one of ordinary skill in the art to which this invention belongs.

Reference to the phrase "at least one of", when such phrase modifies a plurality of items or components (or an enumerated list of items or components) means any combination of one or more of those items or components. For example, the phrase "at least one of A, B, and C" means: (i) A; (ii) B; (iii) C; (iv) A, B, and C; (v) A and B; (vi) B and C; or (vii) A and C.

In understanding the scope of the present disclosure, the term "comprising" and its derivatives, as used herein, are intended to be open-ended terms that specify the presence of the stated features, elements, components, groups, integers, and/or steps, but do not exclude the presence of other unstated features, elements, components, groups, integers and/or steps. The foregoing also applies to words having similar meanings such as the terms, "including", "having" and their derivatives. Also, the terms "part," "section," "portion," "member" "element," or "component" when used in the singular can have the dual meaning of a single part or a plurality of parts. As used herein, the following directional terms "forward, rearward, above, downward, vertical, horizontal, below, transverse, laterally, and vertically" as well as any other similar directional terms refer to those positions of a device or piece of equipment or those directions of the device or piece of equipment being translated or moved.

Finally, terms of degree such as "substantially", "about" and "approximately" as used herein mean the specified value or the specified value and a reasonable amount of deviation from the specified value (e.g., a deviation of up to ±0.1%, ±1%, ±5%, or ±10%, as such variations are appropriate) such that the end result is not significantly or materially changed. For example, "about 1.0 cm" can be interpreted to mean "1.0 cm" or between "0.9 cm and 1.1 cm." When terms of degree such as "about" or "approximately" are used to refer to numbers or values that are part of a range, the term can be used to modify both the minimum and maximum numbers or values.

This disclosure is not intended to be limited to the scope of the particular forms set forth, but is intended to cover alternatives, modifications, and equivalents of the variations or embodiments described herein. Further, the scope of the disclosure fully encompasses other variations or embodiments that may become obvious to those skilled in the art in view of this disclosure.

I claim:

1. An adjustable static-focus intraocular lens, comprising:
an optic portion; and
a peripheral portion coupled to the optic portion,
wherein the peripheral portion comprises a composite material comprising an energy absorbing constituent and a plurality of expandable components, wherein the expandable components are expandable microspheres, and wherein each of the expandable microspheres comprises a blowing agent contained within a thermoplastic shell, and
wherein a base power of the optic portion is configured to change in response to an external energy directed at the composite material.

2. The adjustable static-focus intraocular lens of claim 1, wherein the base power of the optic portion is configured to change between about 0.05 D to about 0.5 D in either a positive or negative direction in response to pulses of the external energy directed at the composite material.

3. The adjustable static-focus intraocular lens of claim 1, wherein the external energy is laser light having a wavelength of between about 488 nm to about 650 nm.

4. The adjustable static-focus intraocular lens of claim 1, wherein the external energy is laser light having a wavelength of between about 946 nm to about 1120 nm.

5. The adjustable static-focus intraocular lens of claim 1, wherein the external energy is laser light emitted by a femtosecond laser.

6. The adjustable static-focus intraocular lens of claim 1 wherein the composite material is formed as discrete peripheral components such that directing the external energy at one discrete peripheral component causes a change in the base power of the optic portion and directing the external energy at another discrete peripheral component also causes a change in the base power of the optic portion.

7. The adjustable static-focus intraocular lens of claim 1, wherein the optic portion comprises an optic fluid chamber and the peripheral portion comprises at least one peripheral fluid chamber in fluid communication with the optic fluid chamber.

8. The adjustable static-focus intraocular lens of claim 7, wherein the composite material is configured as a chamber expander, wherein the chamber expander is configured to expand in response to the external energy directed at the chamber expander, wherein expansion of the chamber expander increases a volume of the at least one peripheral fluid chamber, and wherein the base power of the optic portion is configured to decrease in response to the external energy directed at the chamber expander, and wherein the chamber expander is configured as an expandable column extending from a chamber anterior wall to a chamber posterior wall.

9. The adjustable static-focus intraocular lens of claim 7, wherein the composite material is configured as a space-filler, wherein the space-filler is configured to expand in response to the external energy directed at the space-filler, and wherein expansion of the space-filler decreases a volume of the at least one peripheral fluid chamber, and wherein the base power of the optic portion is configured to increase in response to the external energy directed at the space-filler.

10. The adjustable static-focus intraocular lens of claim 7, wherein the peripheral portion is configured as at least one haptic, wherein the at least one peripheral fluid chamber is defined within the at least one haptic, wherein the at least one peripheral fluid chamber extends only partially into the at least one haptic.

11. The adjustable static-focus intraocular lens of claim 1, wherein the energy absorbing constituent is an energy absorbing colorant.

12. The adjustable static-focus intraocular lens of claim 11, wherein the energy absorbing colorant is an azo dye.

13. The adjustable static-focus intraocular lens of claim 11, wherein the energy absorbing colorant is graphitized carbon black.

14. An adjustable static-focus intraocular lens, comprising:
an optic portion; and
a peripheral portion coupled to the optic portion,
wherein the peripheral portion comprises a composite material comprising an energy absorbing constituent and a plurality of expandable components, wherein each of the expandable components comprises a blowing agent contained within a thermoplastic shell, and wherein the blowing agent is expandable, wherein a base power of the optic portion is configured to change in response to an external energy directed at the composite material.

15. The adjustable static-focus intraocular lens of claim 14, wherein the blowing agent is an expandable gas.

16. The adjustable static-focus intraocular lens of claim 14, wherein the blowing agent is a branched-chain hydrocarbon.

17. An adjustable static-focus intraocular lens, comprising:
an optic portion; and
a peripheral portion coupled to the optic portion,
wherein the peripheral portion comprises a composite material comprising an energy absorbing constituent and a plurality of expandable components, wherein each of the expandable components comprises a blowing agent contained within a thermoplastic shell, and wherein the thermoplastic shell is made in part of nitriles or acrylonitrile copolymers, wherein a base power of the optic portion is configured to change in response to an external energy directed at the composite material.

18. The adjustable static-focus intraocular lens of claim 1, wherein the optic portion comprises a light splitting surface profile defined on a lens surface of the optic portion.

19. The adjustable static-focus intraocular lens of claim 18, wherein the light splitting surface profile comprises a plurality of diffractive zones.

* * * * *